United States Patent
Ferrari

(10) Patent No.: US 9,782,397 B2
(45) Date of Patent: Oct. 10, 2017

(54) TREATMENT OF CORNEAL NEOVASCULARIZATION

(75) Inventor: Giulio Ferrari, Milan (IT)

(73) Assignee: IRBM SCIENCE PARK S.P.A., Rome (IT)

(*) Notice: Subject to any disclaimer, the term of this patent is extended or adjusted under 35 U.S.C. 154(b) by 0 days.

(21) Appl. No.: 14/130,042

(22) PCT Filed: Jul. 4, 2012

(86) PCT No.: PCT/EP2012/063067
§ 371 (c)(1),
(2), (4) Date: Dec. 30, 2013

(87) PCT Pub. No.: WO2013/004766
PCT Pub. Date: Jan. 10, 2013

(65) Prior Publication Data
US 2014/0128395 A1 May 8, 2014

Related U.S. Application Data

(60) Provisional application No. 61/504,265, filed on Jul. 4, 2011.

(51) Int. Cl.
*A61K 31/5377* (2006.01)
*A61K 31/4545* (2006.01)
*A61K 45/06* (2006.01)
*A61K 31/453* (2006.01)

(52) U.S. Cl.
CPC ........ *A61K 31/4545* (2013.01); *A61K 31/453* (2013.01); *A61K 31/5377* (2013.01); *A61K 45/06* (2013.01)

(58) Field of Classification Search
CPC .................. A61K 31/4545; A61K 31/5377
See application file for complete search history.

(56) References Cited

U.S. PATENT DOCUMENTS

| | | | |
|---|---|---|---|
| 5,538,982 | A | 7/1996 | Hagan et al. |
| 5,691,336 | A | 11/1997 | Dorn et al. |
| 5,719,147 | A | 2/1998 | Dorn et al. |
| 6,048,859 | A | 4/2000 | Dorn et al. |
| 6,096,742 | A | 8/2000 | Crocker et al. |
| 6,235,735 | B1 | 5/2001 | Dorn et al. |

FOREIGN PATENT DOCUMENTS

| | | |
|---|---|---|
| WO | WO2008/049842 A2 | 5/2008 |
| WO | WO2009106486 A1 | 9/2009 |
| WO | WO2011061622 A1 | 5/2011 |

OTHER PUBLICATIONS

Bahatti et al., Regression of Corneal Neovascularization (Pak J Ophthamol, 2010, vol. 26.No. 1).*
Gitter et al., European Journal of pharmacology molecular pharmacology section 289 (1995), 439-446.*
Munoz, M., et al., "The Broad-spectrum Antitumor Action of Cyclosporin A is Due to its Tachykinin Receptor Antagonist Pharmacological Profile," Peptides (2010) 31, p. 1643-1648.
Ziche, M., et al., "Substance P Stimulates Neovascularization In Vivo and Proliferation of Cultured Endothelial Cells," Microvascular Research (1990) 40, p. 264-278.
Benelli, U., et al., "Corneal Neovascularization Induced by Xenografts or Chemical Cautery," Invest Opthalmol Vis. Sci (1997) 38, p. 274-282.
Fan, T.P.D., et al., "P49 Inhibition of Substance P-induced Angiogenesis in the Rat by NK-1 Receptor Antagonists," Neuropeptides (1993) 24(4), p. 209.
Seegers, H.C., et al., "Enhancement of Angiogenesis by Endogenous Substance P Release and Neurokinin-1 Receptors During Neurogenic Inflammation," Journal of Pharmacology and Experimental Therapeutics (2003) 306(1), p. 8-12.
F. Bignami, "NK1 Receptor Antagonists as a New, . . . ," Invest Ophthalmol Vis Sci., 2014, V55 No. 10, p. 6783-6794, The Association for Research in Vision and Ophthalmology, Inc.
J. Gottsch, "Topical Cyclosporin Stimulates Neovascularization in Resolving Sterile Rheumatoid Central Corneal . . . ,"Tr. Am. Ophth. Soc., 2000, V98, p. 81-90.
J. Hale, "Structural Optimization Affording 2-(R)-(1-(R)-3,5-Bis(trifluoromethyl) phenylethoxy) . . . ," J. Med. Chem., 1998, V41 No. 23, p. 4607-4614, American Chemical Society.
C.S.J Walpole, "Comparative, general pharmacology of SDZ NKT 343 a novel, selective . . . ," British Journal of Pharmacology, 1998, V124, p. 83-92, Stockon Press.
Hazlett. "Spantide I decreases type I cytokines, enhances IL-10, and reduces corneal . . . " Invest. Opthalmol. Vis. Sci. 2007, 48(2), 797-807.
Fan. "Stimulation of angiogenesis by substance P and interleukin-1 in the rat . . . " Brit. J. Pharmacol. 1993, 110(1), 43-49.
Gupta. "Treatments for Corneal Neovascularization: A Review; Cornea" 2011, 30(8), 927-938.
Tedesco, Dustin. "Cyclosporine: A Review", Journal of Transportation, 2012, v12, p. 1-7, Hindawi Publishing Corporation.

* cited by examiner

*Primary Examiner* — Zohreh Fay
(74) *Attorney, Agent, or Firm* — Birch, Stewart, Kolasch & Birch, LLP

(57) ABSTRACT

There is provided inter alia a compound which is an NK-1 receptor antagonist for use in the treatment or prevention of CNV. There is also provided a compound which is an NK-1 antagonist for use in the treatment of chemical burns of the eye particularly alkali burns of the eye. There is also provided a pharmaceutical composition for topical administration to the eye comprising an NK-1 antagonist and an antibiotic agent.

9 Claims, 9 Drawing Sheets

TREATMENT OF CORNEAL NEOVASCULARIZATION

RELATED APPLICATIONS

This Application is a National Stage Application of International Application No. PCT/EP2012/063067, filed 4 Jul. 2012; which claims the benefit of Provisional Application Ser. No. US61/504,265, filed 4 Jul. 2011; all of which are incorporated herein by reference in their entireties.

BACKGROUND TO THE INVENTION

Corneal Neovascularization

The cornea is a transparent avascular tissue of the eye, whose transparency is essential for clarity of vision. Corneal neovascularization (CNV) is a pathology characterized by the excessive growth of blood vessels from the limbus into adjacent corneal tissues in which the new blood vessels can extend into superficial and deep corneal stroma. As well as having adverse impact on the transparency of the tissue due to the existence of the blood vessels themselves, the infiltrative growth of new blood vessels can disrupt or destroy ocular tissue resulting in widespread adverse effects.

Thus, CNV is characterized by angiogenesis which, by definition, is the formation of new blood vessels. However, CNV can be viewed as being a pathology of complex origin.

CNV is commonly associated with extended wearing of hydrogel contact lenses, presumably as a consequence of oxygen deprivation to the eye.

CNV can develop following trachoma (*Chlamydia trachomatis* infection), infectious keratitis including herpes simplex keratitis, viral interstitial keratitis, infections caused by *staphylococcus, streptococcus, Pseudomonas* or microbial keratoconjunctivitis. CNV as a consequence of ocular *Pseudomonas aeruginosa* infection is discussed in Xue et al (2002) Immunology and Cell Biology 80, 323-327.

CNV is also a sequela of several inflammatory diseases of the anterior segment, such as those resulting from chemical or physical insult of the eye, degenerative and traumatic disorders, dry eye with or without filamentary keratitis, progressive corneal vascularization caused by graft-versus-host disease, limbal stem cell deficiency (including idiopathic, traumatic, aniridia, autoimmune polyendocrinopathy), Stevens-Johnson syndrome, ocular pemphigoid and recurrent pterygium following surgery.

CNV has been associated with allergic conjunctivitis.

It follows from the above discussion that a suitable therapeutic approach to prevention or treatment of CNV will require addressing not only the role of angiogenesis in the condition but also the role of these other factors too, especially inflammation.

The sequelae of CNV are numerous. Thus, CNV can lead to corneal scarring, edema (swelling), lipid deposits, and inflammation that may result in vision loss. In addition, it can lead to loss of immune privilege of the eye which can affect the outcome of corneal transplantation, and worsens the prognosis of penetrating keratoplasty. In turn, corneal transplant is a treatment that many patients with severe corneal disease may ultimately need.

Current Therapies for CNV

To date, several surgical methods have been adopted for controlling CNV. Surgical methods include diathermy, for example fine needle diathermy i.e. the destruction of newly formed bold vessels in the cornea (Thatte S Nepal J Ophthalmol. 2011; 3(5):23-6) and laser photocoagulation, which seems to be effective in a subset of CNV. In the latter case a high recurrence rate has been observed. Complications also include increased inflammation which is obviously undesirable.

Photodynamic therapy has been proposed; this involves the administration of a photosensitizing compound, selectively absorbed by neovascular tissue. Activation of this compound with low energy laser light generates cytotoxic mediators, which cause selective thrombosis and destruction of newly formed vessels.

Corticosteroids have been a standard treatment for CNV. with variable and limited success. Ocular side effects commonly observed include cataract induction, glaucoma, and increased risk of infection (Jones R, 3rd, et al, Curr Opin Ophthalmol 2006; 17:163-7; McGhee C N, et al, Drug Saf 2002; 25:33-55, James E R. J Ocul Pharmacol Ther 2007; 23:403-20.)

New generation corticosteroids with broad angiostatic activities have been developed and constitute a potential therapy for CNV. One example, anecortave acetate, has been shown to be effective in animal models of CNV, as reported by Shakiba et al (2009) Recent Patents on Inflammation and Allergy Drug Discovery 3, 221-231

The anti-VEGF monoclonal antibody bevacizumab has been tested in humans showing some effect following topical administration in inhibiting CNV (Kim S W, et al. Ophthalmology 2008; 115:e33-8, Dastjerdi et al (2009) Arch Ophthalmol 127(4) 381-389.)

The anti-VEGF monoclonal antibody bevacizumab has been tested in humans showing some effect following topical administration in inhibiting CNV (Dastjerdi et al (2009) Arch Ophthalmol 127(4) 381-389). More generally the role of anti-VEGF agents as potential treatments for CNV is discussed in Shakiba et al (2009) supra).

Cyclosporin A, an immunosuppressive drug, is widely used to prevent rejection in corneal transplants. There have been reports of its effective topical use in treatment of CNV following penetrating keratoplasty to treat a fungal corneal ulcer (Sonmez B et al (2009) Int Ophthalmol. 29(2), 123-5). Topical cyclosporin A has been shown to inhibit CNV following xenografts or chemical cautery in rats (Benelli et al (1997) Invest Ophthalmol Vis Sci 38(2) 274-282). Confusingly there are also reports of cyclosporine A stimulating neovascularization in resolving sterile rheumatoid central corneal ulcers (Gottsch and Akpek (2000) Trans Am Ophthalmol Soc. 98, 81-90). Another immunosuppressive drug, rapamycin, has been shown to be effective in inhibition of CNV in a murine corneal alkaline burn model of the disease (Kwon Y S et al (2005) Invest Ophthalmol Vis Sci. 46(2), 454-60).

In unconnected disclosures, cyclosporin A, is reported to be an NK-1 receptor antagonist (Gitter et al (1995)289(3), 439-46) and it is reported that cyclosporin A has selectivity for both NK-1 and NK-2 (Munoz et al (2010) Peptides 31, 1643-8).

Bearing in mind the complex pharmacology exhibited by cyclosporin A, it has never been suggested that the potential efficacy of cyclosporin A in treating CNV is in any way connected with its NK-1 antagonist activity.

Substance P

Substance P is a C-amidated decapeptide that belongs, along with neurokinin-A, neurokinin-B, and neuropeptide-K, to the tachykinin family. The tachykinin receptor system belongs to the GPCR superfamily and comprises three subtypes of receptors, namely NK1, NK2, NK3. The principal receptor for substance P is NK-1.

Substance P is abundantly expressed in central, peripheral, and enteric nervous systems. It is also present in the peripheral sensory nerves of the cornea (Muller and Tervo (2003) Exp Eye Res, 76, 521-542).

Corneal vascularization has traditionally been studied in animal models in the field of neovascular research to test angiogenic and anti-angiogenic substances. The visibility, accessibility and avascularity of the cornea are highly advantageous and facilitate the biomicroscopic grading of the neovascular response upon topical application of test substances (Kenyon B M et al, Invest. Ophthalmol. Vis. Sci. 1996, 37; (8) 1625-1632).

In this context, Ziche et al (Ziche and Maggi (1990) Microvascular Research 40, 264-278) investigated the role of Substance P on the growth of capillary vessels in vivo and on the proliferation of cultured endothelial cells. They implanted slow release pellets containing substance P into the avascular cornea of rabbits and monitored vessel growth observing that Substance P induced a marked neovascularization and a selective NK-1 agonist also induced neovascularisation. The authors also showed that Substance P increased proliferation of endothelial cells in vitro. Moreover, a selective NK-1 agonist increased proliferation of endothelial cells in vitro whereas a selective NK-2 agonist and a selective NK-3 agonist had no significant effect.

While Ziche et al assert a direct role of Substance P in the process of neovascularization as a proangiogenic factor, their perspective was to look at neovascularization of the cornea as a convenient model of angiogenesis and they were not concerned with a physiological role of Substance P in the cornea. For example, on page 276 they state that "Further studies are needed to assess whether under in vivo conditions SP [Substance P] or other tachykinins acting on NK1 receptors can gain access to endothelial cells in concentrations relevant to exert a proliferative effect on them in such a way as to stimulate new vessel formation". Furthermore, their experimental settings were such as to avoid the presence of inflammatory stimuli which are a well known underlying cause of the pathology of CNV in humans (see for instance page 268: "The present experiments were performed with doses of peptides which did not produce overt signs of inflammation"). Hence at no point is it suggested by Ziche et al that antagonizing the action of Substance P might be of therapeutic use in the prevention or treatment of CNV.

NK-1 Antagonists

Over 300 patents have been filed in the past two decades in the NK1 antagonist field (Huan et al (2010) Expert Opinion therapeutic patents 20(8): 1019-1045), with compounds under investigation and development for various diseases, from depression to cancer.

The only compound approved thus far for use in therapy is aprepitant and its water soluble injectable form, fosaprepitant dimeglumine, a phosphorylated prodrug which is rapidly converted to aprepitant in vivo following intravenous administration for the prevention of acute and delayed nausea and vomiting associated with cancer chemotherapy

SUMMARY OF THE INVENTION

The inventors have now invented a novel treatment which is efficacious in treating and preventing CNV.

According to the invention there is provided a compound which is an NK-1 antagonist for use in the treatment or prevention of CNV. There is also provided a method of treatment or prevention of CNV which comprises administering to a subject in need thereof, for example an animal subject and especially a human subject, a therapeutically effective amount of an NK-1 antagonist. There is also provided use of an NK-1 antagonist in the manufacture of a medicament for the treatment or prevention of CNV.

In another aspect the invention there is provided a compound which is an NK-1 antagonist for use in the treatment of chemical burns of the eye particularly alkali burns of the eye. There is also provided a method of treatment of chemical burns of the eye particularly alkali burns of the eye which comprises administering to a subject in need thereof, for example an animal subject and especially a human subject, a therapeutically effective amount of an NK-1 antagonist. There is also provided use of an NK-1 antagonist in the manufacture of a medicament for the treatment of chemical burns of the eye particularly alkali burns of the eye. Treatment of acid burns of the eye is also contemplated.

DETAILED DESCRIPTION OF THE INVENTION

Conditions

Figure 1:
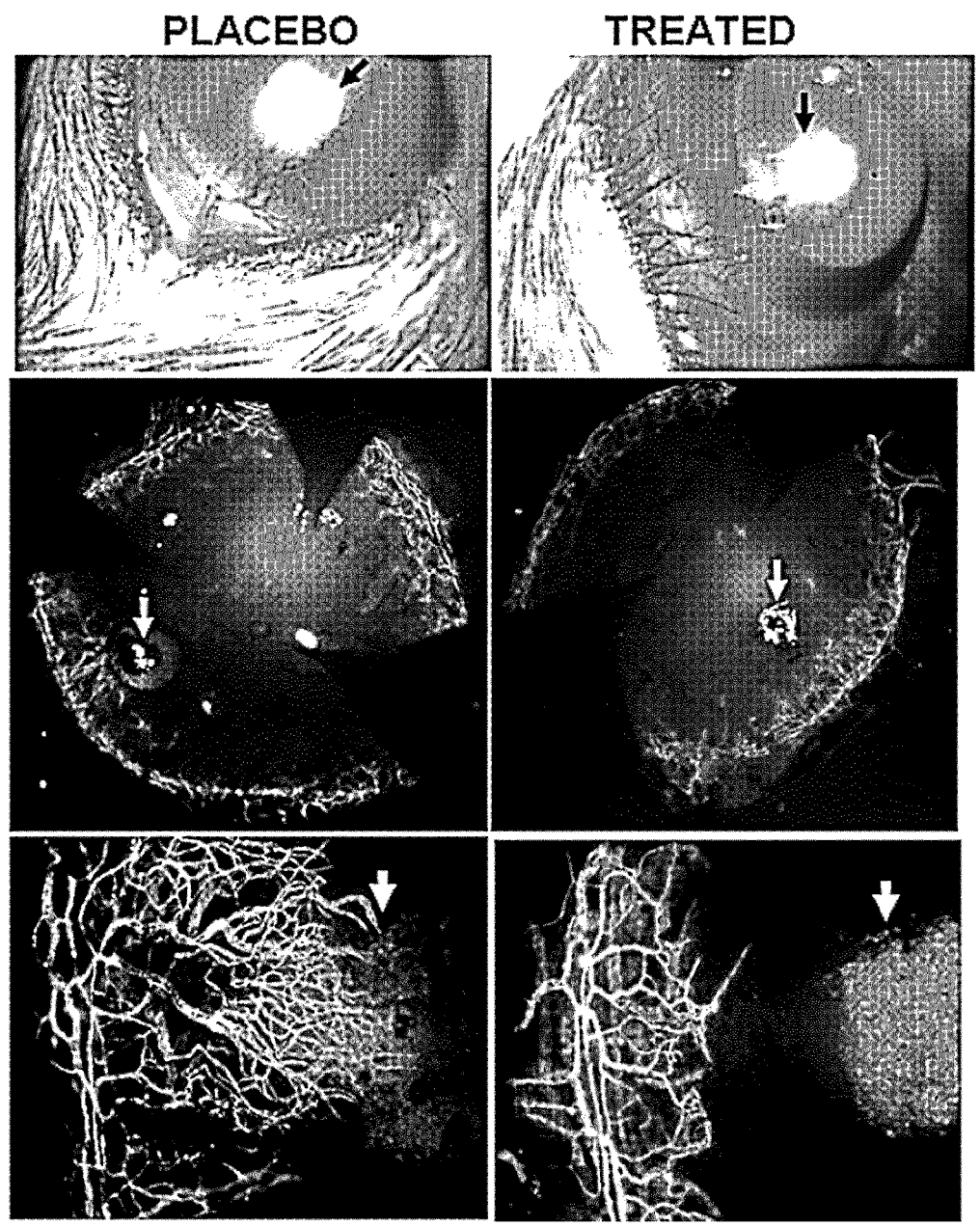
FIG. 1. Topical application of fosaprepitant reduces corneal neovascularization in a mouse micropocket angiogenesis assay.

According to the present invention the treatment or prevention of CNV includes the treatment, amelioration or prevention of medical conditions of the eye characterized by the presence of neovascularization of the cornea.

As noted above, corneal neovascularization is a sequel of several inflammatory and infectious diseases of the eye inter alia.

Hence in an embodiment, the NK-1 antagonist may be used for treatment or prevention of CNV associated with or consequential to inflammatory disorders such as ocular pemphigoid, atopic conjunctivitis, rosacea, graft rejection, Lyell's syndrome, Stevens-Johnson syndrome, graft versus host disease; Infectious keratitis including viral keratitis such as keratitis caused by infection with herpes simplex or herpes zoster, bacterial keratitis such as keratitis caused by infection with *Pseudomonas* (e.g. *Pseudomonas Aeruginosa*), *Chlamydia trachomatis, Treponema pallidum*), fungal keratitis such as keratitis caused by *Candida, Fusarium* and *Aspergillus* spp and parasitic keratitis such as keratitis caused by Onchocerciasi; degenerative disorders including congenital disorders such as pterygium, Terrien's marginal degeneration and aniridia; traumatic disorders such as ulcerations, acid burns, alkali burns; trauma associated with medical or surgical procedures; disorders associated with extended contact lens wear; and stem cell deficiency (e.g. of limbus).

The treatment scheme may be prophylactic, thus the treatment may be administered to individuals at risk of acquiring the conditions described herein.

Accordingly, in a preferred embodiment, the invention provides a method for preventing corneal neovascularization in a subject in need thereof, including the steps of: (a) identifying the subject at risk of neovascularization; and (b) administering to the cornea of the subject an NK-1 antagonist thereby preventing neovascularization of the cornea.

An aspect of the invention provides a compound which is an NK-1 antagonist for use in the treatment of chemical burns of the eye e.g. alkali or acid burns particularly alkali burns of the eye, especially of the cornea. In particular, it provides an NK-1 antagonist having one or more of the following specific benefits following or associated with chemical burns of the eye particularly alkali burns of the eye: reduction in scarring of the eye, reduction in inflammation of the eye, reduction in corneal perforation and preservation of or improvement in anatomical integrity of adnexa of the eye (e.g. eyelids) (including reduction in incidence of symblepharon and ankyloblepharon) following chemical burns of the eye e.g. alkali or acid burns particularly alkali burns of the eye.

Neurokinin-1 Antagonists:

NK-1 antagonists may, for example, have an inhibitory concentration (IC50) against the human NK-1 receptor in competition with substance P of less than 100 μM eg less than 10 μM eg less than 1 μM eg less than 100 nM eg less than 10 nM, as measured by Radiolabeled ligand binding assay on human cells transfected with NK-1 receptor (see for instance Walpole et al, British Journal of Pharmacology (1998); 124:83-92)

NK-1 antagonists are suitably selective antagonists, NK-1 antagonists are suitably selective for NK-1 over other receptors, especially NK-2 and NK-3. Thus NK-1 antagonists may, for example, have an inhibitory concentration (IC50) against the human NK-2 receptor in competition with Neurokinin A which is at least 10 times greater than the inhibitory concentration (IC50) against the human NK-1 receptor in competition with substance P (i.e. it is at least 10 fold selective for NK1 over NK-2), eg at least 50 fold eg at least 100 times selective for NK-1 over NK-2. NK-1 antagonists may, for example, have an inhibitory concentration (IC50) against the human NK-3 receptor in competition with Neurokinin B which is at least 10 times greater than the inhibitory concentration (IC50) against the human NK-1 receptor in competition with substance P (i.e. it is at least 10 fold selective for NK1 over NK-3), eg at least 50 times eg at least 100 fold selective for NK-1 over NK-3.

IC50 values against NK-1, NK-2 and NK-3 receptors may be determined as shown in Walpole et al, supra, by radiolabelled ligand binding assay of human cells transfected with NK1, NK2 or NK3 receptors.

In an embodiment the NK-1 antagonist is selected from the list consisting of:
a. Aprepitant (MK-0869L-754,030), IUPAC name 5-([(2R,3S)-2-((R)-1-[3,5-bis(trifluoromethyl)phenyl]ethoxy)-3-(4-fluorophenyl)morpholino]methyl)-1H-1,2,4-triazol-3(2H)-one,

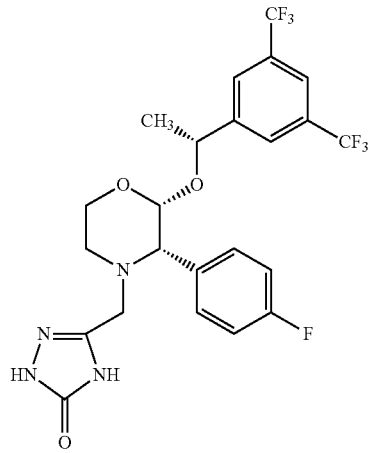 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

as described and claimed in the following US patents: U.S. Pat. Nos. 5,719,147, 5,538,982, 6,048,859, 6,096,742 and 6,235,735, the contents of which are incorporated herein by reference in their entirety. Also described in: Hale J J et al, J Med Chem 1998; 41 (23) 4607-14; as well as pro-drugs thereof, such as:

Fosaprepitant (L-758,298, Emend) IUPAC name [3-{[(2R,3S)-2-[(1R)-1-[3,5-bis(trifluoromethyl)phenyl]ethoxy]-3-(4-fluorophenyl)morpholin-4-yl]methyl}-5-oxo-2H-1,2,4-triazol-1-yl]phosphonic acid

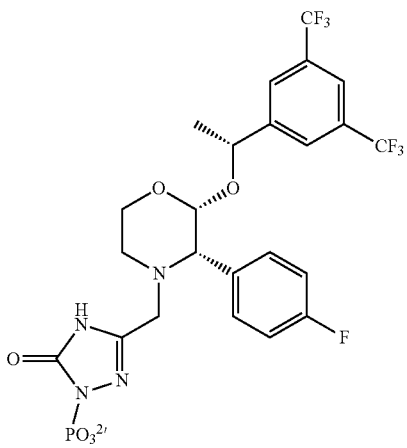

e.g. in the form of a salt such as the dimeglumine salt as described and claimed at least in U.S. Pat. No. 5,691,336, the contents of which are incorporated herein by reference in its entirety;

b. ZD4974 as described in WO02026724 and WO01077089, the contents of which are incorporated herein by reference in its entirety:

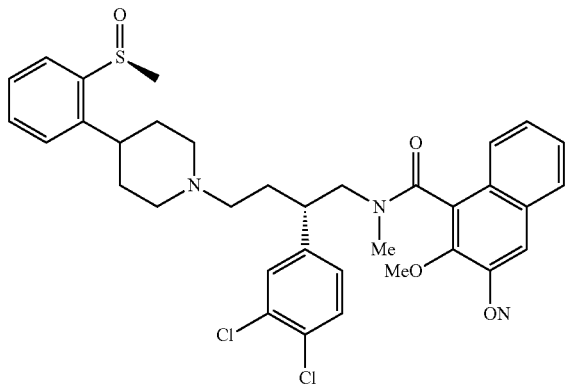

c. The following compound, described in WO01077069 and WO00059873, the contents of which are incorporated herein by reference in entirety:

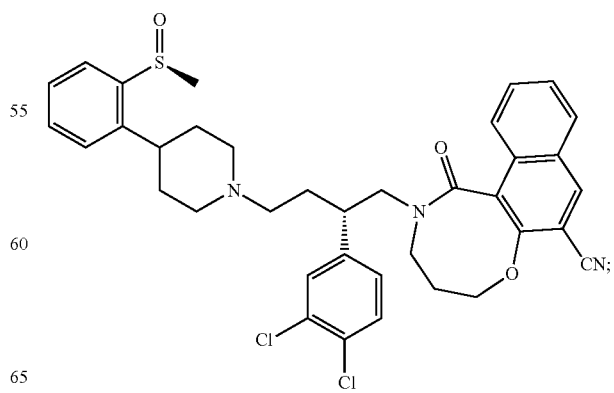

d. The following compound described in DE19519245, the contents of which are incorporated herein by reference in its entirety:

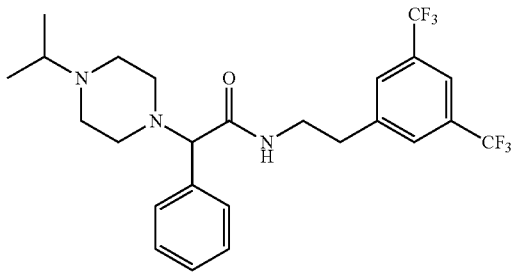 [SMILES: CC(C)N1CCN(C(C(=O)NCCc2cc(C(F)(F)F)cc(C(F)(F)F)c2)c2ccccc2)CC1]

e. The following compound described in WO9732865, the contents of which are incorporated herein by reference in its entirety:

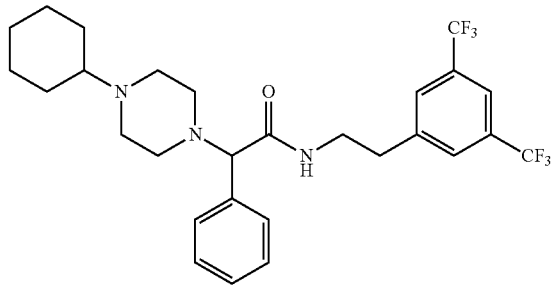 [SMILES: O=C(NCCc1cc(C(F)(F)F)cc(C(F)(F)F)c1)C(c1ccccc1)N1CCN(C2CCCCC2)CC1]

f. The following compound described in EP1295599, the contents of which are incorporated herein by reference in its entirety:

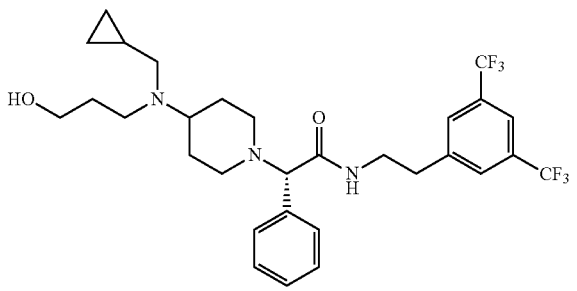 [SMILES: O=C(NCCc1cc(C(F)(F)F)cc(C(F)(F)F)c1)[C@H](c1ccccc1)N1CCC(N(CCCO)CC2CC2)CC1]

g. CGP49823 described in WO9626183 and WO9610562, the contents of which are incorporated herein by reference in their entirety:

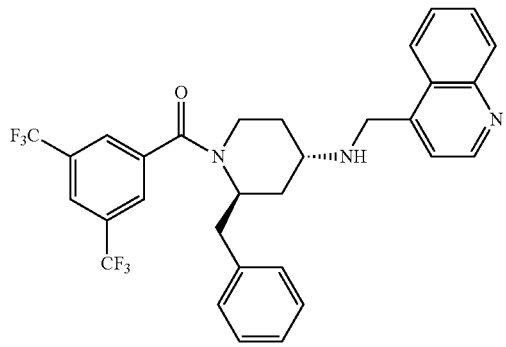 [SMILES: O=C(c1cc(C(F)(F)F)cc(C(F)(F)F)c1)N1CC[C@H](NCc2ccnc3ccccc23)C[C@H]1Cc1ccccc1]

h. The following compound as described in WO9514017, the contents of which are incorporated herein by reference in its entirety:

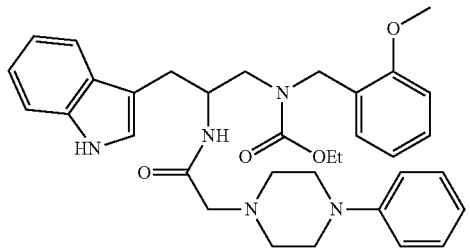 [SMILES: CCOC(=O)N(Cc1ccccc1OC)CC(Cc1c[nH]c2ccccc12)NC(=O)CN1CCN(c2ccccc2)CC1]

i. LY303870, Lanepitant, described in WO9907681, the contents of which are incorporated herein by reference in its entirety:

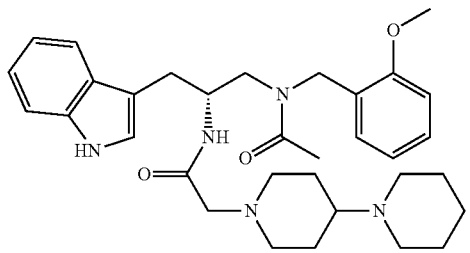 [SMILES: COc1ccccc1CN(C[C@@H](Cc1c[nH]c2ccccc12)NC(=O)CN1CCC(N2CCCCC2)CC1)C(C)=O]

j. LI 686017, described in WO03091226, the contents of which are incorporated herein by reference in its entirety:

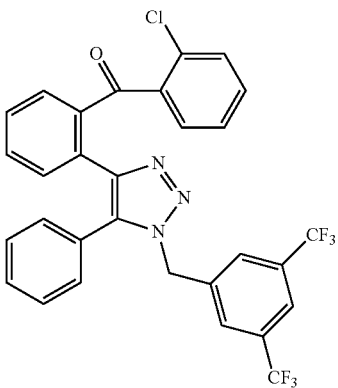

k. FK888, as described in Hagiwara D et al, J Med Chem 1994; 37: 2090-9 and WO9222569, WO9314113, WO9321215, EP655442 and WO9637488, the contents of which are incorporated herein by reference in their entirety:

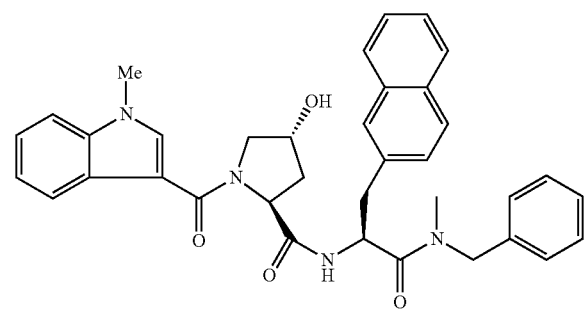 [SMILES: CN(Cc1ccccc1)C(=O)[C@H](Cc1ccc2ccccc2c1)NC(=O)[C@@H]1C[C@@H](O)CN1C(=O)c1cn(C)c2ccccc12]

l. The following compound, described in WO9222569, WO9314113, WO9321215, EP655442 and WO9637488, the contents of which are incorporated herein by reference in their entirety:

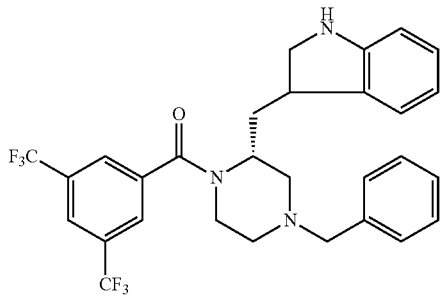 [SMILES: O=C(c1cc(C(F)(F)F)cc(C(F)(F)F)c1)N1CCN(Cc2ccccc2)C[C@H]1CC1CNc2ccccc21]

m. The following compound, described in WO9222569, WO9314113, WO9321215, EP655442 and WO9637488, the contents of which are incorporated herein by reference in their entirety:

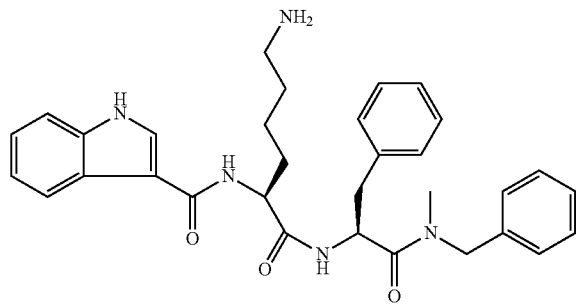 [SMILES: CN(Cc1ccccc1)C(=O)[C@H](Cc1ccccc1)NC(=O)[C@H](CCCCN)NC(=O)c1c[nH]c2ccccc12]

n. The following compound, described in WO00053572, the contents of which are incorporated herein by reference in its entirety:

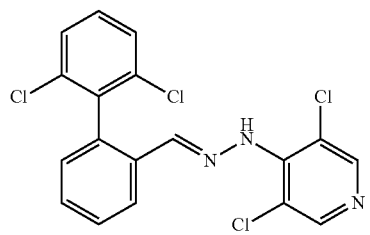 [SMILES: Clc1cncc(Cl)c1N/N=C/c1ccccc1-c1c(Cl)cccc1Cl]

o. Netupitant, described in WO020008232, the contents of which are incorporated herein by reference in its entirety:

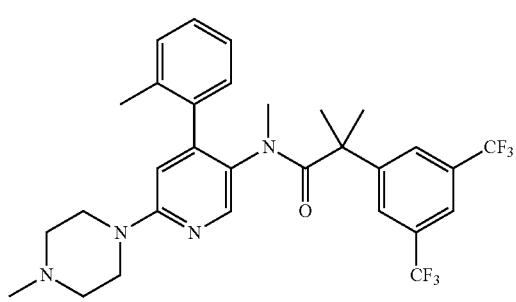 [SMILES: Cc1ccccc1-c1cc(N2CCN(C)CC2)ncc1N(C)C(=O)C(C)(C)c1cc(C(F)(F)F)cc(C(F)(F)F)c1]

p. Befetupitant, described in WO020008232, the contents of which are incorporated herein by reference in its entirety:

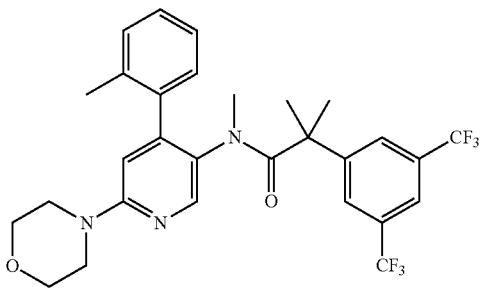 [SMILES: Cc1ccccc1-c1cc(N2CCOCC2)ncc1N(C)C(=O)C(C)(C)c1cc(C(F)(F)F)cc(C(F)(F)F)c1]

q. The following compound, described in WO202062784 and WO020008232, the contents of which are incorporated herein by reference in their entirety:

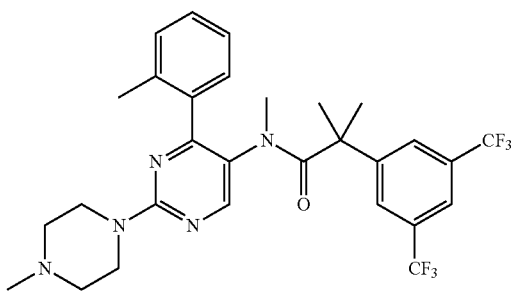 [SMILES: Cc1ccccc1-c1nc(N2CCN(C)CC2)ncc1N(C)C(=O)C(C)(C)c1cc(C(F)(F)F)cc(C(F)(F)F)c1]

r. R116031, described in WO9724356 and WO0716440, the contents of which are incorporated herein by reference in their entirety:

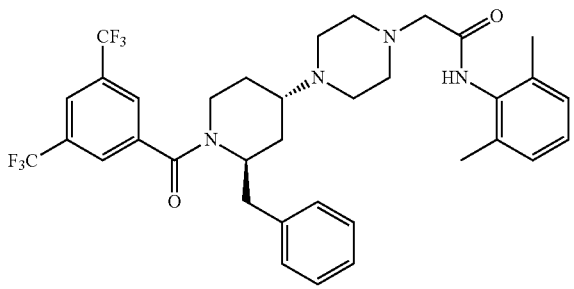 [SMILES: Cc1cccc(C)c1NC(=O)CN1CCN([C@H]2CCN(C(=O)c3cc(C(F)(F)F)cc(C(F)(F)F)c3)[C@H](Cc3ccccc3)C2)CC1]

s. The following compound, described in EP522808, the contents of which are incorporated herein by reference in its entirety:

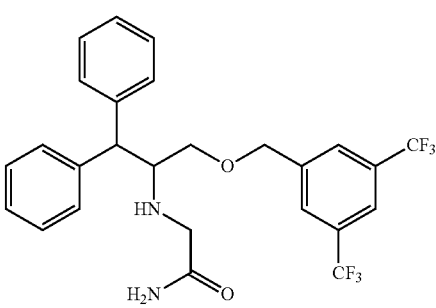 [SMILES: NC(=O)CNC(COCc1cc(C(F)(F)F)cc(C(F)(F)F)c1)C(c1ccccc1)c1ccccc1]

t. The following compound:

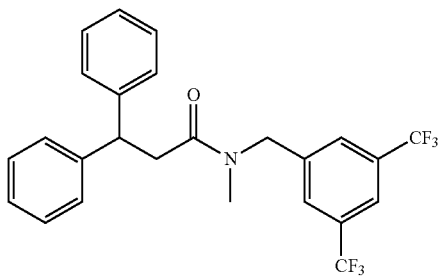 [SMILES: CN(Cc1cc(C(F)(F)F)cc(C(F)(F)F)c1)C(=O)CC(c1ccccc1)c1ccccc1]

u. L733,060

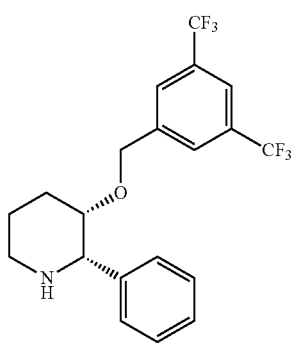 [SMILES: FC(F)(F)c1cc(CO[C@H]2CCCN[C@H]2c2ccccc2)cc(C(F)(F)F)c1]

v. L736,281

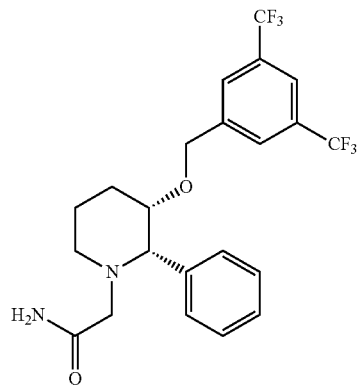 [SMILES: NC(=O)CN1CCC[C@H](OCc2cc(C(F)(F)F)cc(C(F)(F)F)c2)[C@@H]1c1ccccc1]

w. TKA731, described in WO9831704, the contents of which are incorporated herein by reference in its entirety:

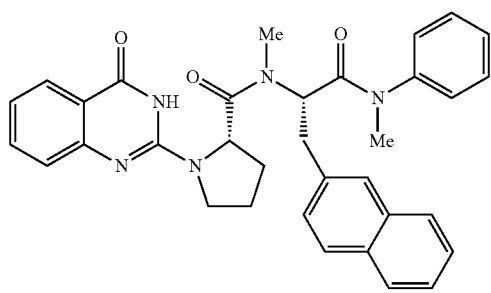 [SMILES: CN(C(=O)[C@H](Cc1ccc2ccccc2c1)N(C)C(=O)[C@@H]1CCCN1c1nc2ccccc2c(=O)[nH]1)c1ccccc1]

x. NKP608, described in WO04024714, the contents of which are incorporated herein by reference in its entirety:

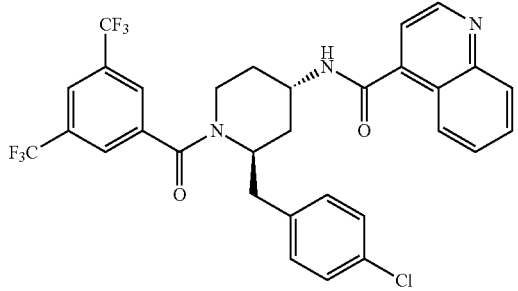 [SMILES: O=C(N[C@H]1CCN(C(=O)c2cc(C(F)(F)F)cc(C(F)(F)F)c2)[C@H](Cc2ccc(Cl)cc2)C1)c1ccnc2ccccc12]

y. CP96,345 described in Lowe J A et al. 1992; 35:2591-600, and in WO92021677, the contents of which are incorporated herein by reference in their entirety;

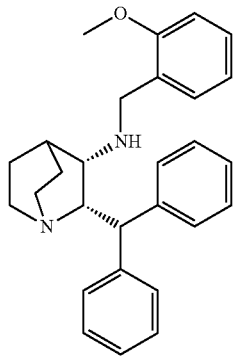 [SMILES: COc1ccccc1CN[C@H]1C2CCN(CC2)[C@H]1C(c1ccccc1)c1ccccc1]

z. The following compound, described in Lowe J A et al. J Med Chem 1994; 37:2831-40, and in WO92021677, the contents of which are incorporated herein by reference in their entirety;

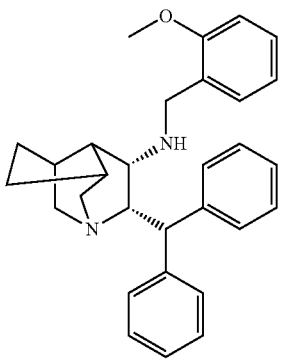 [SMILES: COc1ccccc1CN[C@H]1C2C3CCC2CN(C3)[C@H]1C(c1ccccc1)c1ccccc1]

aa. CP99,994, described in Desai M C et al. J Med Chem 1992; 35:4911-3, the contents of which are incorporated herein by reference in its entirety;

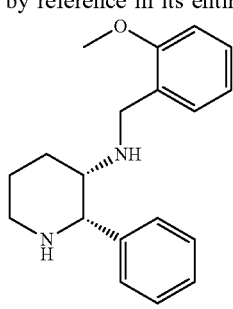

bb. CP-122,721 described in Rosen T J et al. Bioorg Med Chem Lett 1998; 8:281-4, the contents of which are incorporated herein by reference in its entirety:

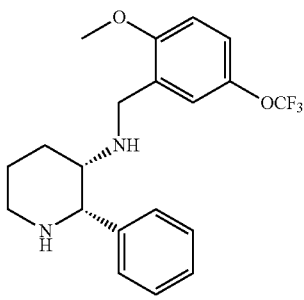 [SMILES: COc1ccc(OC(F)(F)F)cc1CN[C@H]1CCCN[C@H]1c1ccccc1]

cc. CJ-17,493, described in WO9925714, the contents of which are incorporated herein by reference in its entirety:

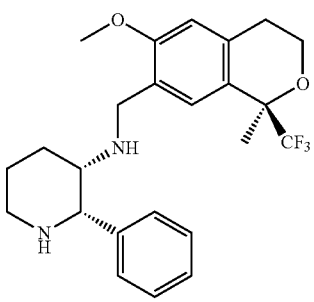 [SMILES: COc1cc2c(cc1CN[C@H]1CCCN[C@H]1c1ccccc1)[C@](C)(C(F)(F)F)OCC2]

dd. Ezlopitant, CJ-11,974 described in WO1992021677 the contents of which are incorporated herein by reference in its entirety:

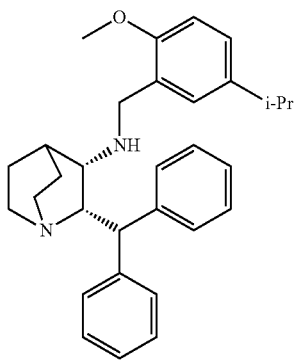 [SMILES: COc1ccc(C(C)C)cc1CN[C@H]1C2CCN(CC2)[C@H]1C(c1ccccc1)c1ccccc1]

ee. Maropitant, CJ-11,972, described in WO1992021677, U.S. Pat. Nos. 6,222,038 and 6,255,230, the contents of which are incorporated herein by reference in their entirety:

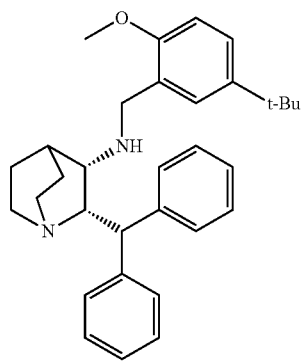 [SMILES: COc1ccc(C(C)(C)C)cc1CN[C@H]1C2CCN(CC2)[C@H]1C(c1ccccc1)c1ccccc1]

ff. RP77580 described in EP429366, the contents of which are incorporated herein by reference in its entirety:

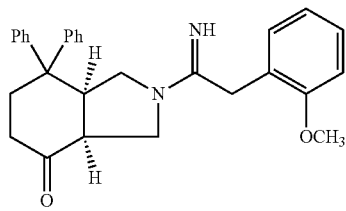 [SMILES: COc1ccccc1CC(=N)N1C[C@H]2C(=O)CCC(c3ccccc3)(c3ccccc3)[C@H]2C1]

gg. Dapitant, RPR100893, described in WO9321154, the contents of which are incorporated herein by reference in its entirety:

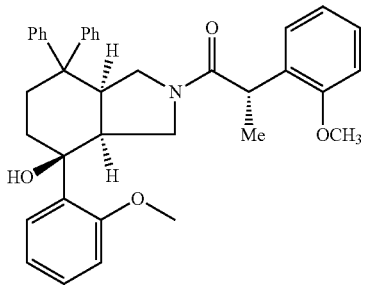 [SMILES: COc1ccccc1[C@H](C)C(=O)N1C[C@@H]2[C@H](C1)C(c1ccccc1)(c1ccccc1)CC[C@@]2(O)c1ccccc1OC]

hh. The following compound, described in EP512901, the contents of which are incorporated herein by reference in its entirety:

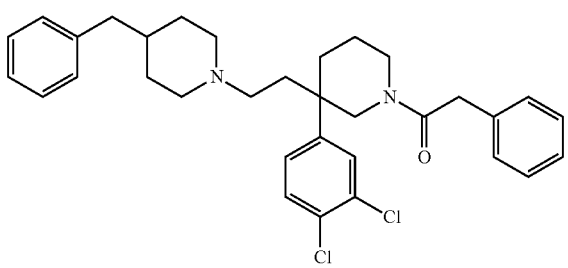 [SMILES: O=C(Cc1ccccc1)N1CCCC(CCN2CCC(Cc3ccccc3)CC2)(c2ccc(Cl)c(Cl)c2)C1]

ii. Nolpitantium, SR140333 described in EP512901, the contents of which are incorporated herein by reference in its entirety:

$IC_{50} = 8.3$ nM

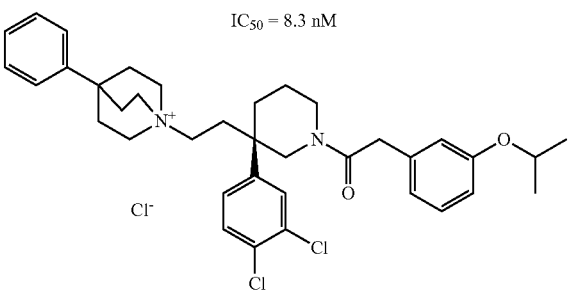 [SMILES: CC(C)Oc1cccc(CC(=O)N2CCC[C@](CC[N+]34CCC(c5ccccc5)(CC3)CC4)(c3ccc(Cl)c(Cl)c3)C2)c1 ; [Cl-]]

jj. The following compound, described in WO9526338, the contents of which are incorporated herein by reference in its entirety:

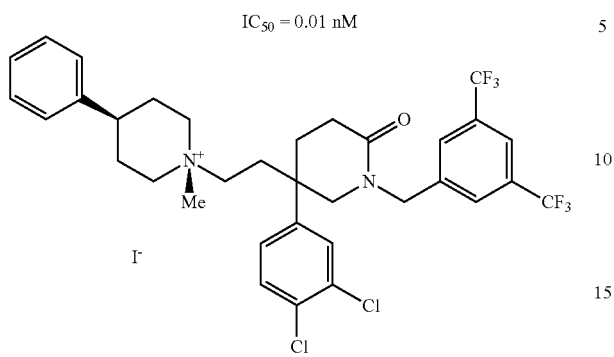

kk. SSR240600, described in WO00068292, the contents of which are incorporated herein by reference in its entirety:

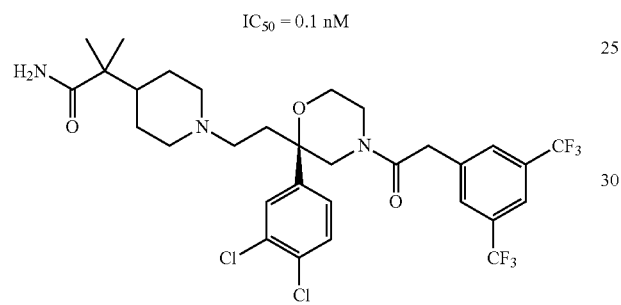

ll. SCH388714 described in WO06065654, the contents of which are incorporated herein by reference in its entirety:

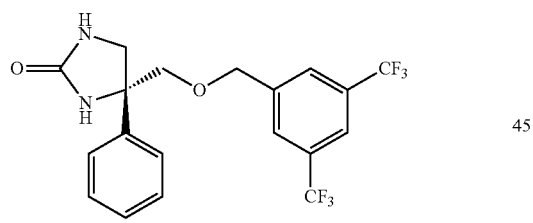

mm. The following compound described in Paliwal S et al, Bioorg Med Chem Lett 2008; 18:4168-71, the contents of which are incorporated herein by reference in its entirety:

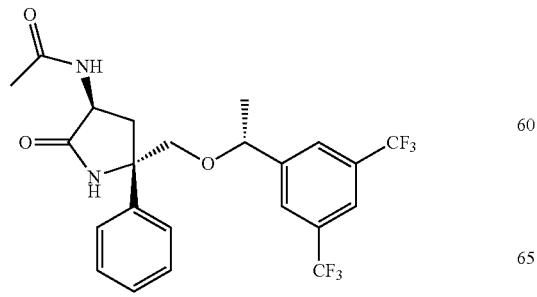

nn. Rolapitant, described in WO03051840, the contents of which are incorporated herein by reference in its entirety:

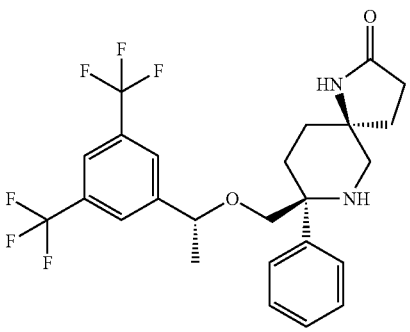 [SMILES: C[C@@H](OC[C@@]1(c2ccccc2)CC[C@]2(CCC(=O)N2)CN1)c1cc(C(F)(F)F)cc(C(F)(F)F)c1]

oo. The following compound, described in EP566069, the contents of which are incorporated herein by reference in its entirety:

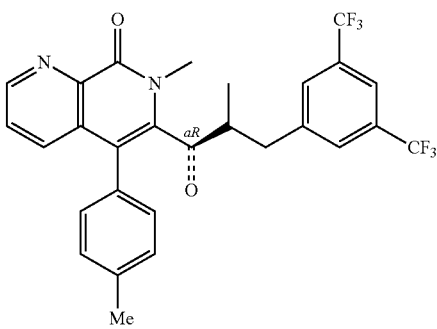

pp. TAK-637, described in JP10259184, the contents of which are incorporated herein by reference in its entirety:

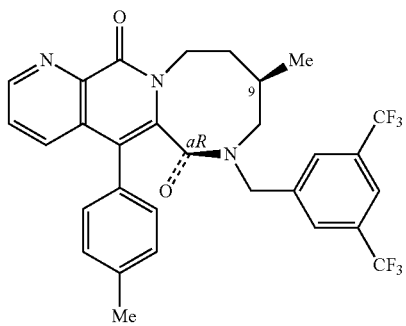

qq. The following compound described in JP2004002334, the contents of which are incorporated herein by reference in its entirety:

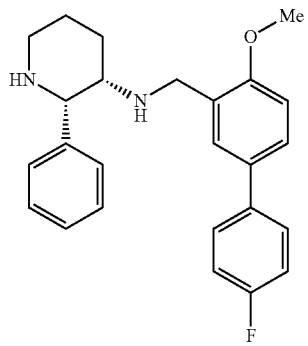 [SMILES: COc1ccc(-c2ccc(F)cc2)cc1CN[C@H]1CCCN[C@H]1c1ccccc1]

rr. The following compound described in JP2007277231 and JP2008239618, the contents of which are incorporated herein by reference in their entirety:

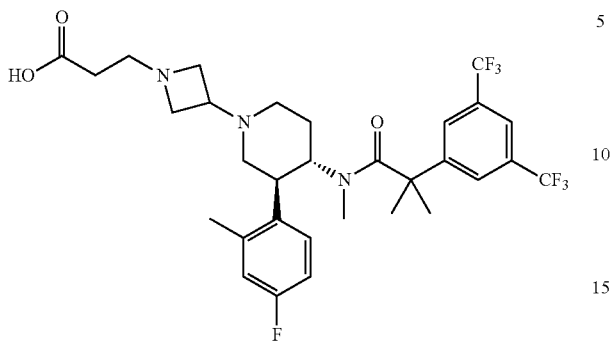

ss. The following compound described in JP2007277231 and JP2008239618, the contents of which are incorporated herein by reference in their entirety:

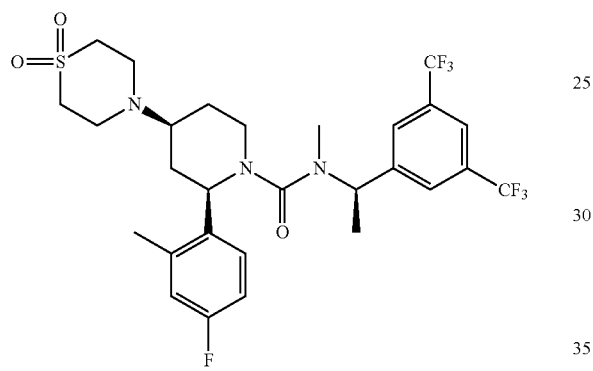

tt. The following compound described in WO9317032 and WO9511686, the contents of which are incorporated herein by reference in their entirety:

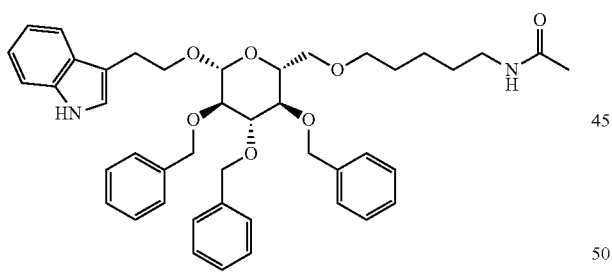

uu. The following compound described in WO9630367 and WO01025233, the contents of which are incorporated herein by reference in their entirety:

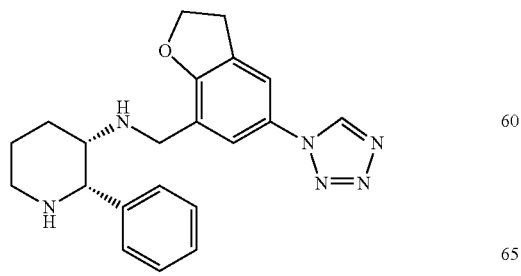

vv. HSP117 described in WO9630367 and WO01025233, the contents of which are incorporated herein by reference in their entirety:

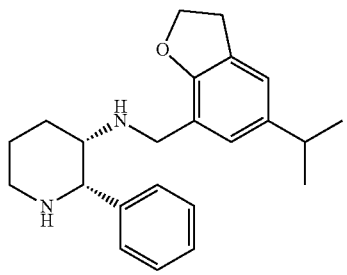 [SMILES: CC(C)c1cc2c(c(CN[C@H]3CCCN[C@H]3c3ccccc3)c1)OCC2]

ww. The following compound, described in Set S, et al. Bioorg Med Chem ILKett 2005; 15:1479-84 and WO03062245, the contents of which are incorporated herein by reference in their entirety:

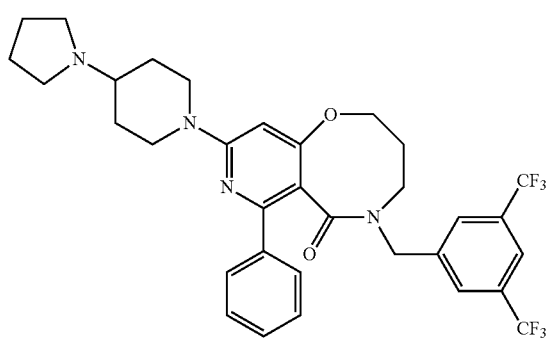 [SMILES: O=C1c2c(cc(N3CCC(N4CCCC4)CC3)nc2-c2ccccc2)OCCCN1Cc1cc(C(F)(F)F)cc(C(F)(F)F)c1]

xx. The following compound, described in Seto S, et al. Bioorg Med Chem Lett 2005; 15:1479-84 and WO03062245, the contents of which are incorporated herein by reference in their entirety:

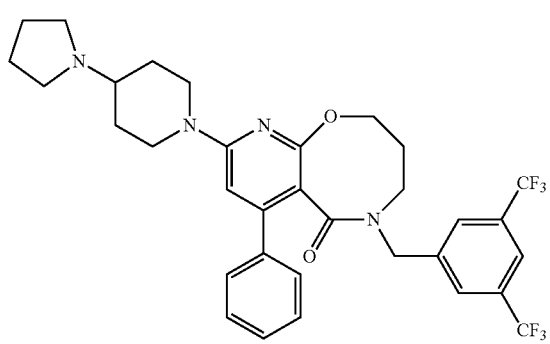 [SMILES: O=C1c2c(-c3ccccc3)cc(N3CCC(N4CCCC4)CC3)nc2OCCCN1Cc1cc(C(F)(F)F)cc(C(F)(F)F)c1]

yy. The following compound, KRP-103, described in WO03062245 and WO05019225, the contents of which are incorporated herein by reference in their entirety:

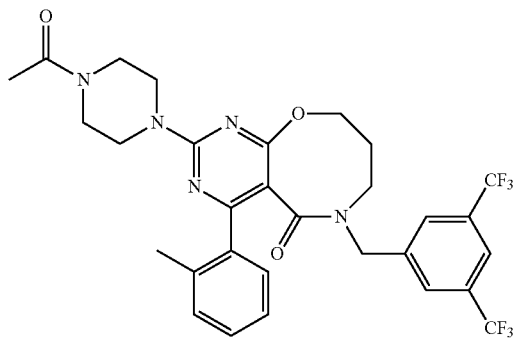 [SMILES: CC(=O)N1CCN(c2nc3c(c(-c4ccccc4C)n2)C(=O)N(Cc2cc(C(F)(F)F)cc(C(F)(F)F)c2)CCCO3)CC1]

zz. The following compound described in WO06106727, the contents of which are incorporated herein by reference in its entirety:

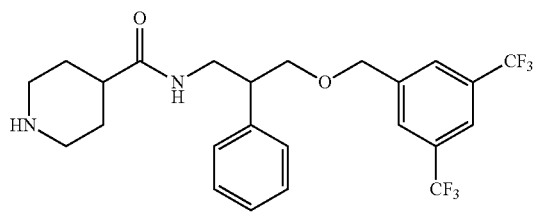 [SMILES: O=C(NCC(COCc1cc(C(F)(F)F)cc(C(F)(F)F)c1)c1ccccc1)C1CCNCC1]

aaa. The following compound, described in WO07074491, the contents of which are incorporated herein by reference in its entirety:

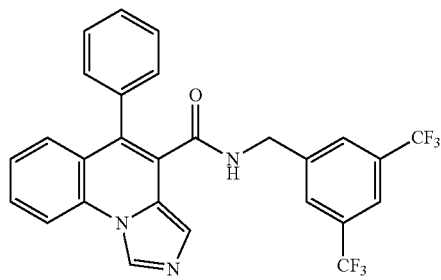 [SMILES: O=C(NCc1cc(C(F)(F)F)cc(C(F)(F)F)c1)c1c(-c2ccccc2)c2ccccc2n2cncc12]

bbb. SLV317, described in US20020065276, the contents of which are incorporated herein by reference in its entirety:

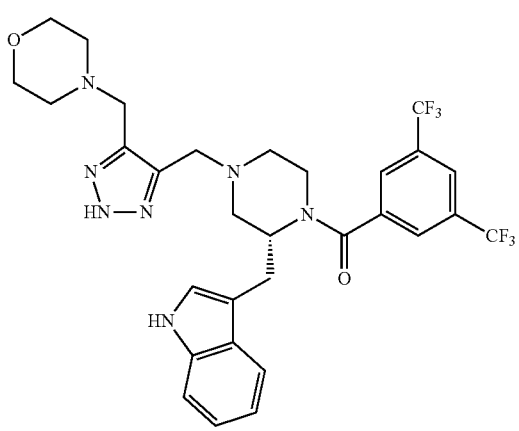 [SMILES: O=C(c1cc(C(F)(F)F)cc(C(F)(F)F)c1)N1CCN(Cc2n[nH]nc2CN2CCOCC2)C[C@H]1Cc1c[nH]c2ccccc12]

ccc. Compounds of formula I described in WO9508549, the contents of which are incorporated herein by reference in its entirety:

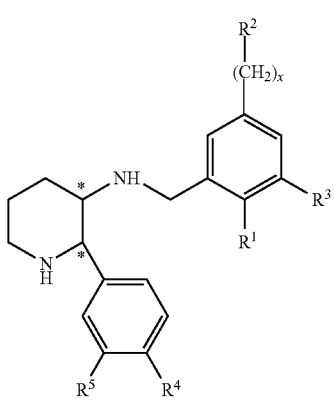

wherein $R^1$ is a $C_{1-4}$ alkoxy group;
$R^2$ is

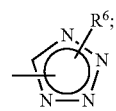

$R^3$ is a hydrogen or halogen atom;
$R^4$ and $R^5$ may each independently represent a hydrogen or halogen atom, or a $C_{1-4}$alkoxy or trifluoromethyl group;
$R^6$ is a hydrogen atom, a phenyl, $NR^7R^8$, $CH_2C(O)CF_3$ or trifluoromethyl group;
$R^7$ and $R^8$ may each independently represent a hydrogen atom, or a or acyl group;
x represents zero or 1;
n represents zero, 1 or 2;
m represents zero or 1.

ddd. Compounds of formula II described in WO9629326, the contents of which are incorporated herein by reference in its entirety:

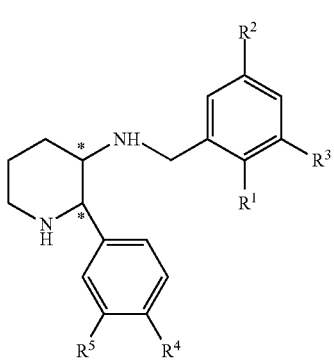

wherein $R^1$ is a C2-4alkoxy group;
$R^2$ is

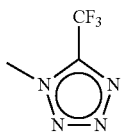

$R^3$ is a hydrogen or halogen atom;
$R^4$ and $R^5$ may each independently represent a hydrogen or halogen atom, or a or trifluoromethyl group;

including Vofopitant, (2S,3S)-N-[[2-methoxy-5-[5-(trifluoromethyl)tetrazol-1-yl]phenyl]methyl]-2-phenylpiperidin-3-amine, described in WO9629326, the contents of which are incorporated herein by reference in its entirety:

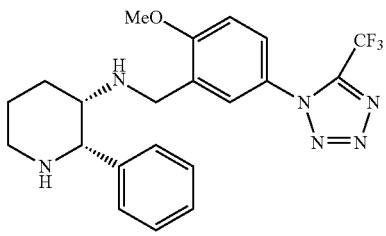 [SMILES: COc1ccc(-n2nnnc2C(F)(F)F)cc1CN[C@H]1CCCN[C@H]1c1ccccc1]

eee. Compounds of formula III as described in WO01025219, the contents of which are incorporated herein by reference in its entirety:

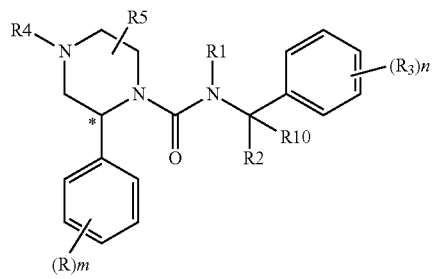

wherein:
R represents a halogen atom or a C1-4 alkyl group;
R1 represents hydrogen or a C1-4 alkyl group;
R2 represents hydrogen, a C-.4alkyl, C-alkyl or a C3 7 cycloalkyl group; or R1 and R2 together with nitrogen and carbon atom to which they are attached respectively represent a 5-6 membered heterocyclic group;
R3 represents a trifluoromethyl, a C1 4 alkyl, a C1 4 alkoxy, a trifluoromethoxy or a halogen group;
R4 represents hydrogen, a (CH2) qR7 or a (CH2) rCO(CH2) pR7 group;
R5 represents hydrogen, a C1-4 alkyl or a COR6 group;
R6 represents hydrogen, hydroxy, amino, methylamino, dimethylamino a 5 membered heteroaryl group containing 1 to 3 heteroatoms selected from oxygen, sulphur and nitrogen or a 6 membered heteroaryl group containing 1 to 3 nitrogen atoms;
R7 represents hydrogen, hydroxy or NR8R9 wherein R8 and R9 represent independently hydrogen or C1-4 alkyl optionally substituted by hydroxy, or by amino;
R10 represents hydrogen;
m is zero or an integer from 1 to 3; n is zero or an integer from 1 to 3;
both p and r are independently zero or an integer from 1 to 4; q is an integer from 1 to 4;
including Vestipitant, (2S)-N-[(1R)-1-[3,5-bis(trifluoromethyl)phenyl]ethyl]-2-(4-fluoro-2-methylphenyl)-N-methylpiperazine-1-carboxamide, described in WO01025219 the contents of which are incorporated herein by reference in its entirety:

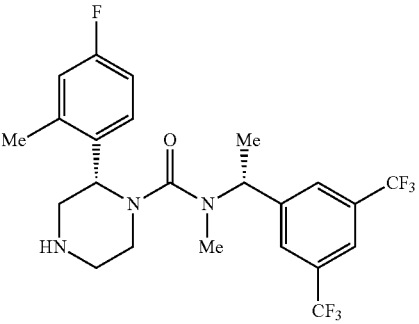 [SMILES: Cc1cc(F)ccc1[C@H]1CNCCN1C(=O)N(C)[C@H](C)c1cc(C(F)(F)F)cc(C(F)(F)F)c1]

fff. Compounds of formula IV described in WO03066635, the contents of which are incorporated herein by reference in its entirety:

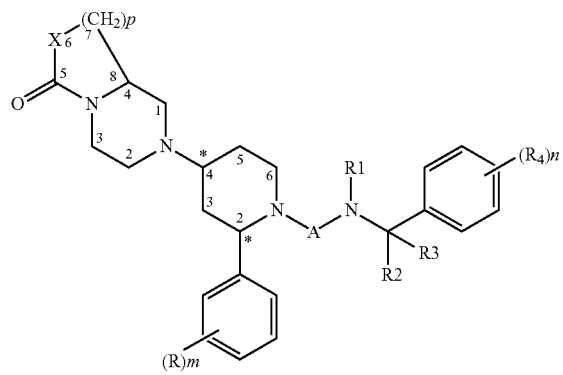

wherein
R represents halogen or C1-4 alkyl R1 represents C1 4 alkyl;
R2 or R3 independently represent hydrogen or C1 4 alkyl;
R4 represents trifluoromethyl, C1-4 Alkyl, C1 4 alkoxy, trifluoromethoxy or halogen; Rs represents hydrogen, C1-4 alkyl or C3 7 cycloalkyl; R6 is hydrogen and R7 is a radical of formula (W): or R6 is a radical of formula (W) and R7 is hydrogen; X represents CH2, NRs or O; Y represents Nitrogen and Z is CH or Y represents CH and Z is Nitrogen; A represents C(O) or S(O)q, provided that when Y is nitrogen and Z is CH, A is not S(O)q; m is zero or an integer from 1 to 3; n is an integer from 1 to 3; p and q are independently an integer from 1 to 2;
Including the following named compounds:

Orvepitant (GW823296): (2R,4S)-N-{(1R)-1-[3,5-bis(trifluoromethyl)phenyl]ethyl}-2-(4-fluoro-2-methylphenyl)-N-methyl-4-[(8aS)-6-oxohexahydro-1H-pyrrolo-[1,2-a]pyrazin-2-yl]piperidine-1-carboxamide, alternatively identified as 2-(R)-(4-Fluoro-2methyl-phenyl)-4-(S)-((8aS)-6-oxo-hexahydro-pyrrolo[1-,2-a]-pyrazin-2-yl)-piperidine-1-carboxylic acid[1-(R)-(3,5-bis-trifluoromethyl-phenyl)-ethyl]-methylamide maleate

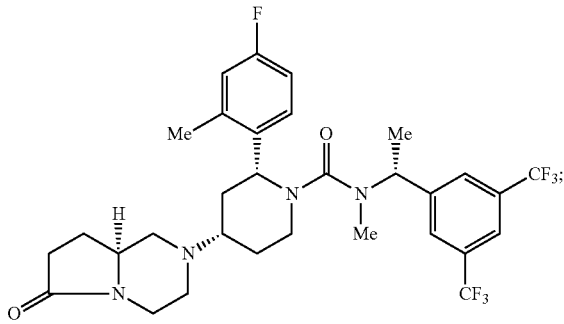 [SMILES: Cc1cc(F)ccc1[C@H]1C[C@@H](N2CCN3C(=O)CC[C@H]3C2)CCN1C(=O)N(C)[C@H](C)c1cc(C(F)(F)F)cc(C(F)(F)F)c1]

2-(R)-(4-Fluoro-2-methyl-phenyl)-4-(S)-(6-oxo-hexahydro-pyrrolo[1,2-a]-pyrazin-2-yl)-piperidine-1-carboxylic acid (3,5-bis-trifluoromethyl-benzyl)-methylamide;
2-(R)-(4-Fluoro-2-methyl-phenyl)-4-(S)-(6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide;
1-(4-Fluoro-2-methyl-phenyl)-4-(6-oxo-hexahydro-pyrrolo[1,2-a]pyrazin-2-yl)-piperidine-2-carboxylic acid (3,5-bis-trifluoromethyl-benzyl)-methylamide;
2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide,
2-(R)-(4-Fluoro-2-methyl-phenyl)-4-(S)-((8aR)-6-oxo-hexahydro-pyrrolo[1,2-a]-pyrazin-2-yl)-piperidine-1-carboxylic acid[1-(R)-(3,5-bis-trifluoromethyl-phenyl)-ethyl]-methylamide, ggg. Compounds of formula V as described in WO02032867, the contents of which are incorporated herein by reference in its entirety:

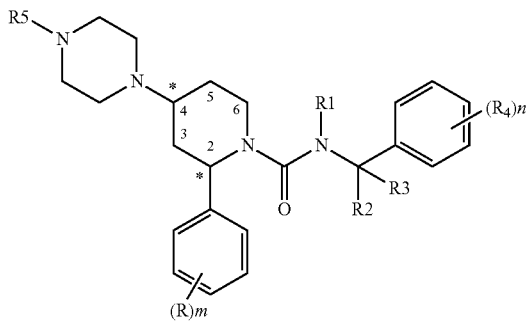

wherein R represents a halogen atom or a C1-4 alkyl group;
R1 represents a Cul-4 alkyl group;
R2 represents hydrogen or a C1-4 alkyl group;
R3 represents hydrogen or C1-4 alkyl group;
R4 represents a trifluoromethyl group;
R5 represents hydrogen, a C1-4 alkyl group or C(O)R6;
R6 represents C1-4 alkyl, C3-7 cycloalkyl, NH(C1-4 alkyl) or N(C1-4alkyl)2;
m is zero or an integer from 1 to 3; n is an integer from 1 to 3;

including the following named compounds:
Casopitant, (2S,4S)-4-(4-Acetyl-1-piperazinyl)-N-[(1R)-1-[3,5-bis(trifluoromethyl)phenyl]ethyl]-2-(4-fluoro-2-methylphenyl)-N-methyl-1-piperidinecarboxamide,

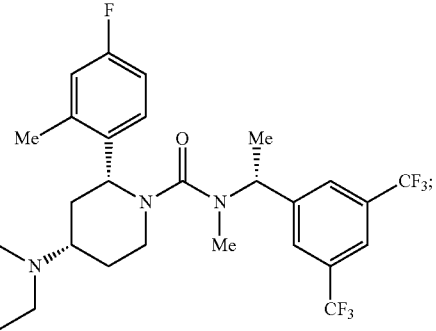

4-(S)-(4-acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;
4-(R)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;
4-(S)-(4-Acetyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]-methylamide;
4-(S)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide;
4-(R)-(4-Acetyl-piperazin-1-yl)-2-(R)-(4-fluoro-2-methyl-phenyl)-piperidine-1-carboxylic acid, (3,5-bis-trifluoromethyl-benzyl)-methylamide;
2-(R)-(4-Fluoro-2-methyl-phenyl)-4-(R,S)-(4-methyl-piperazin-1-yl)-piperidine-1-carboxylic acid, [1-(R)-(3,5-bis-trifluoromethyl-phenyl)-ethyl]-methylamide;
2-(R)-(4-Fluoro-2-methyl-phenyl)-4-(S)-piperazin-1-yl-piperidine-1-carboxylic acid, [1-(R)-(3,5-bis-trifluoromethyl-phenyl)-ethyl]-methylamide;
2-(R)-(4-Fluoro-2-methyl-phenyl)-4-(R,S)-(4-methyl-piperazin-1-yl)-piperidine-1-carboxylic acid, (3,5-bis-trifluoromethyl-benzyl)-methylamide;
4-(S)-(4-Cyclopropanoyl-piperazin-1-yl)-2-(R)-(4-fluoro-2-methyl-phenyl)-piperidine-1-carboxylic acid, [1-(R)-(3,5-bis-trifluoromethyl-phenyl)-ethyl]methylamide;
4-(R)-(4-Cyclopropanoyi-piperazin-1-yi)-2-(R)-(4-fluoro-2-methyl-phenyl)-piperidine-1-carboxylic acid, [1-(R)-(3,5-bis-trifluoromethyl-phenyl)-ethyl]-methylamide;
4-(S)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide;
4-(R)-[4-(2-Methyl-propanoyl)-piperazin-1-yl]-2-(R)-(4-fluoro-2-methyl-phenyl)-piperidine-1-carboxylic acid, [1-(R)-(3,5-bis-trifluoromethyl-phenyl)-ethyl]-methylamide;
4-(S)-[1-[(3,5-Bis-trifluoromethyl-benzyl)-methyl-carbamoyl]-2-(R)-(4-fluoro-2-methyl-phenyl)-piperidin-4-yl]-piperazine-1-carboxylic acid, dimethylamide;
4-(S)-[1-[(3,5-Bis-trifluoromethyl-benzyl)-methyl-carbamoyl]-2-(R)-(4-fluoro-2-methyl-phenyl)-piperidin-4-yl]-1-carboxylic acid, methylamide;
4-(S)-[1-[(3,5-Bis-trifluoromethyl-benzyl)-methyl-carbamoyl]-2-(R)-(4-fluoro-2-methyl-phenyl)-piperidin-4-yl]-piperazine;
4-(S)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide;

4-(R)-(4-Acetyl-piperazin-1-yl)-2-(R)-(4-fluoro-phenyl)-piperidine-1-carboxylic acid, [1-(R)-(3,5-bis-trifluoromethyl-phenyl)-ethyl]-methylamide;

hhh. Compounds of formula VI as described in WO03015784 the contents of which are incorporated herein by reference in its entirety:

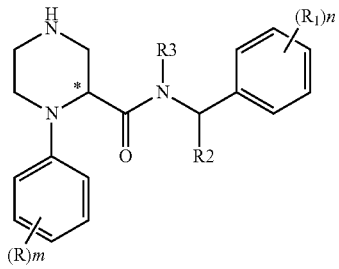

wherein R represents halogen, C1-4 alkyl, trifluoromethoxy or trifluoromethyl;
R1 is trifluoromethyl, C1-4 alkyl, C1-4 alkoxy, halogen or trifluoromethoxy;
R2 is hydrogen, C1-4 alkyl or C2-6 alkenyl;
R3 represents hydrogen or C1 4 alkyl;
n and m are independently 0 or an integer from 1 to 3
including the following named compounds:
(+/−)1-(4-Fluoro-2-methyl-phenyl)-piperazine-2-carboxylic acid, (3,5-bis-trifluoromethyl-benzyl)-methylamide;
(+/−)1-(4-Fluoro-2-methyl-phenyl)-piperazine-2-carboxylic acid (3,5-dichloro-benzyl)-methylamide;
(+/−)I-(4-Fluoro-2-methyl-phenyl)-piperazine-2-carboxylic acid[1-(3,5-dichloro-phenyl)-ethyl]-methylamide;
(+/−)1-(4-Fluoro-2-methyl-phenyl)-piperazine-2-carboxylic acid (3,5-dichloro-benzyl)-(+/−methylamide;
(+/−)I-(4-Fluoro-2-methyl-phenyl)-piperazine-2-carboxylic acid (3,5-bis-trifluoromethyl-benzyl)-methylamide;
(+/−)1-(4-Fluoro-2-methyl-phenyl)-piperazine-2-carboxylic acid (3,4-dibromo-benzyl)-methylamide;
(+/−)I-(4-Trifluoromethyl-phenyl)-piperazine-2-carboxylic acid (3,5-bis-trifluoromethyl-benzyl)-methylamide;
(+/−)1-(4-Fluoro-2-methyl-phenyl)-piperazine-2-carboxylic acid (3,5-dichloro-benzyl)-methylamide;
(+)1-(4-Fluoro-2-methyl-phenyl)-piperazine-2-carboxylic acid (3,5-dichloro-benzyl)-methylamide;
(−)1-(4-Fluoro-2-methyl-phenyl)-piperazine-2-carboxylic acid (3,5-dichloro-benzyl)-methylamide;

iii. Compounds of formula VII as described in WO2005121122, the contents of which are incorporated herein by reference in its entirety:

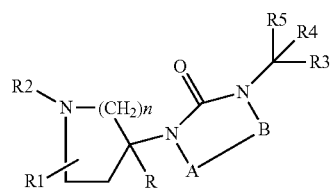

wherein:
R represents a group selected from:

i)

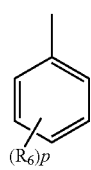

ii)

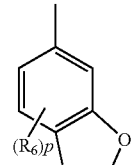

iii)

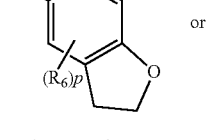

or iv)

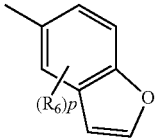

in which R is halogen, cyano, C1-4 alkyl or trifluoromethyl and p is 2 or 3 or R6 is halogen, cyano, C1-4 alkyl, C1-4 alkoxy, trifluoromethoxy or trifluoromethyl and p is 0 or 1;
R1 represents hydrogen, halogen, cyano, C2-4 alkenyl, C1.4 alkyl optionally substituted by halogen, cyano or C1-4 alkoxy;
R2 represents hydrogen or (CH2)qR7;
R3 and R4 each independently are hydrogen or C1.4 alkyl;
R5 represents:
phenyl substituted by 1 to 3 groups independently selected from trifluoromethyl, C1-4 alkyl, cyano, C1-4 alkoxy, trifluoromethoxy, halogen, S(O)rC1-4 alkyl or a phenyl substituted by a 5 or 6 membered heteroaryl group optionally substituted by 1 to 3 groups independently selected from trifluoromethyl, C1-4 alkyl, cyano, C1-4 alkoxy, trifluoromethoxy, halogen or S(O)r C1-4 alkyl;
naphthyl substituted by 1 to 3 groups independently selected from trifluoromethyl, C1-4 alkyl, cyano, C1-4 alkoxy, trifluoromethoxy, halogen or S(O)r C1-4 alkyl;
a 9 to 10 membered fused bicyclic heterocyclic group substituted by 1 to 3 groups independently selected from trifluoromethyl, C1-4 alkyl, cyano, C1-4 alkoxy, trifluoromethoxy, halogen or S(O)r C1-4 alkyl or
R5 is a 5 or 6 membered heteroaryl group substituted by 1 to 3 groups independently selected from trifluoromethyl, C1-4 alkyl, cyano, C-1.4 alkoxy, trifluoromethoxy, halogen or S(O)r C1-4 alkyl;
R7 is hydrogen, C3-7 cycloalkyl, C1.4 alkoxy, amine, C-1.4 alkylamine, (C-1.4 alkyl)2amine, OC(O)NR8Rg9 or C(O)NR8R9;
R8 and R9 each independently represent hydrogen, C1-4 alkyl or C3-7 cycloalkyl;
•A-B is a bivalent radical of formula (v), (vi) or (vii)

—CH═C (R1 1)-     (v)

—C(R10)═CH— or     (vi)

—C(Rˆ)(R1O)—C(Ri I)(R-Ia)—     (vii)

wherein R10, R11, R12 and R13 each independently are hydrogen or C1-4 alkyl; •
n is 1 or 2;
q is an integer from 1 to 4;
r is 1 or 2 including the following named compounds:
1-[(3,5-dichlorophenyl)methyl]-3-[4-(4-fluorophenyl)-1-methyl-4-piperidinyl]-1,3-dihydro-2H-imidazol-2-one;
1-[(3,5-dichlorophenyl)methyl]-3-[4-(4-fluorophenyl)-1-methyl-4-piperidinyl]-1,3-dihydro-2H imidazol-2-one;
1-[(3,5-Dichlorophenyl)methyl]-3-[4-(4-fluorophenyl)-4-piperidinyl]-1,3-dibydro-2H-imidazol-2 one;
1-[1-(3,5-Dichlorophenyl)ethyl]-3-[4-(4-fluorophenyl)-1-methyl-4-piperidinyl]-1,3-dihydro-2H imidazol-2-one;
1-[1-(3-Chloro-1-naphthalenyl)ethyl]-3-[4-(4-fluorophenyl)-1-methyl-4-piperidinyl]-1,3 dihydro-2H-imidazol-2-one;
1-[1-(3,5-Dichlorophenyl)ethyl]-3-[4-(4-fluorophenyl)-1-methyl-4-piperidinyl]-1,3-dihydro-2H imidazol-2-one;
1-[1-(3-Chloro-1-naphthalenyl)ethyl]-3-[4-(4-fluorophenyl)-1-methyl-4-piperidinyl]-1,3 dihydro-2H-imidazol-2-one;
1-[(3,5-dichlorophenyl)methyl]-3-[4-(4-fluorophenyl)-1-methyl-4-piperidinyl]-2 imidazolidinone;
4-({3-[4-(4-fluorophenyl)-1-methyl-4-piperidinyl]-2-oxo-1-imidazolidinyl}methyl)-2 naptthalenecarbonitrile;
7-fluoro-4-({3-[4-(4-fluorophenyl)-1-methyl-4-piperidinyl]-2-oxo-1-imidazolidinyl}methyl)-2 naphthalenecarbonitrile;
6-fluoro-4-({3-[4-(4-fluorophenyl)-1-methyl-4-piperidinyl]-2-oxo-1-imidazolidinyl}methyl)-2 naphthalenecarbonitrile;
1-[(3-chloro-1-naphthalenyl)methyl]-3-[4-(4-fluorophenyl)-1-methyl-4-piperidinyl]-1,3-dihydro 2H-imidazol-2-one;
jjj. A compound of Formula VIII as described in WO2004/005256, the contents of which are incorporated herein by reference in its entirety:

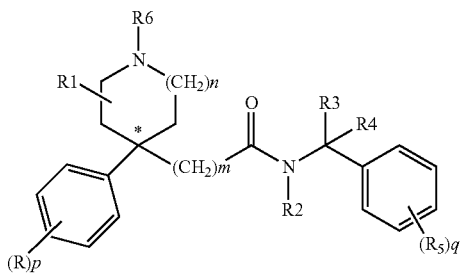

Wherein:
R represents halogen, C1-4 alkyl, cyano, C1-4 alkoxy, trifluoromethyl or trifluoromethoxy;
R1 represents hydrogen, halogen, C3-7cycloalkyl, hydroxy, nitro, cyano or C1-4 alkyl optionally substituted by halogen, cyano or C1-4 alkoxy;
R2 represents hydrogen or C1-4 alkyl;
R3 and R4 independently represent hydrogen, cyano, C1-4 alkyl or R3 together with R4 represents C3-7 cycloalkyl;
R5 represents trifluoromethyl, S(O)tC1-4 alkyl, C1-4 alkyl, C1-4 alkoxy, trifluormethoxy, halogen or cyano R6 represents hydrogen or (CH2) rR7;
R7 represents hydrogen, C3-7 cycloalkyl, NH(C1-4alkylOC1-4alkoxy), NH(C1-4alkyl), NH(C1-4alkyl)2, OC(O)NR9R8, NR8C(O)5R9 or C(O) NR8R9;
R8 and R9 independently represent hydrogen, C1-4 alkyl or C37 cycloalkyl;
m is zero or an integer from 1 to 4;
n represents 1 or 2;
p is zero or an integer from 1 to 3;
q is an integer from 1 to 3;
r is an integer from 1 to 4; tis 0, 1 or 2 provided that when m is 0, p is 2, q, r and n represent 1, R1, R2, R3, R4, R5 and R7 are hydrogen and R is chlorine, R5 is not iodine
including the following named compounds:
N-(3,5-Dichlorobenzyl)-2-[3-fluoro-4-(4-fluorophenyl)-piperidin-4-yl]-N-methyl-acetamide;
4-(4-Fluorophenyl)-piperidine-4-carboxylic acid, (3,5-bis-trifluoromethyl-benzyl)-methylamide;
4-(4-Chlorophenyl)-piperidine-4-carboxylic acid, (3,5-bis-trifluoromethyl-benzyl)-methylamide;
4-(4-Fluorophenyl)-piperidine-4-carboxylic acid (3,5-dichloro-benzyl)-methylamide;
N-(3,5-Bis-trifluoromethyl)-benzyl-2-[(4-fluoro-2-methyl-phenyl)-piperidin-4-yl]-N-methyl-acetamide;
N-(3,5-Dichlorobenzyl)-2-[4-(4-fluoro-2-methyl-phenyl)-piperidin-4-yl]-N-methyl-acetamide;
N-(3,5-Bis-trifluoromethyl-benzyl)-2-[4-(4-fluorophenyl)-azepin-4-yi]-N-methyl-acetamide;
N-(3,5-Bis-trifluoromethyl-benzyl)-2-[4-(4-fluoro-2-methyl-phenyl)-azepin-4-yl]-N-methyl-acetamide;
N-(3,5-Dichlorobenzyl)-2-[4-(4-fluoro-2-methyl-phenyl)-azepin-4-y]-N-methyl-acetamide
N-(3,5-Bis-trifluoromethyl-benzyl)-2-[3-fluoro-4-(4-fluoro-2-methyl-phenyl)-azepin-4-yl]-N-methyl-acetamide;
N-(3,5-Dichlorobenzyl)-2-[3-fluoro-4-(4-fluoro-2-methyl-phenyl)-azepin-4-yi]-N-methyl-acetamide;
N-(3,5-Dichlorobenzyl)-2-[3-fluoro-4-(4-fluoro-2-methyl-phenyl)-azepin-4-yl]-N-methyl-acetamide;
N-(3,5-Bis-trifluoromethyl-benzyl)-2-[3-fluoro-4-(4-fluoro-2-methyl-phenyl)-azepin-4-yl]-N-methyl-acetamide;
N-(3,5-Dibromobenzyl)-2-[4-(4-fluorophenyl)-piperidin-4-yl]-N-methyl-acetamide;
N-(3,5-Dibromo-benzyl)-2-[4-(4-fluoro-phenyl)-1-methyl-piperidin-4-yl]-N-methyl-acetamide;
N-(3,5-Dibromobenzyl)-2-(4-phenyl-piperidin-4-yl)-N-methyl-acetamide;
N-(3,5-Dibromo-benzyl)-2-(4-phenyl-1-methyl-piperidin-4-yl)-N-methyl-acetamide;
N-[1-(3,5-Dichloro-phenyl)-ethyl]-2-[4-(4-fluoro-phenyl)-piperidin-4-yl]-N-methyl-acetamide;
N-[1-(3,5-Dichloro-phenyl)-ethyl]-2-[4-(4-fluoro-phenyl)-1-methyl-piperidin-4-yl]-N-methyl-acetamide;
N-[1-(3,5-Bis-trifluoromethyl-phenyl)-ethyl]-2-[4-(4-fluoro-phenyl)-piperidin-4-yl]-N-methyl-acetamide;
N-[1-(3,5-Bis-trifluoromethyl-phenyl)-ethyl]-2-[4-(4-fluoro-phenyl)-1-methyl-piperidin-4-yl]-N-methyl-acetamide;
N-[1-(3,5-Dibromo-phenyl)-ethyl]-2-[4-(4-fluoro-phenyl)-piperidin-4-yl]-N-methyl-acetamide;
N-[1-(3,5-Dibromo-phenyl)-ethyl]-2-[4-(4-fluoro-phenyl)-1-methyl-piperidin-4-yl]-N-methyl-acetamide;
N-[1-(3,5-Bis-trifluoromethyl-phenyl)-ethyl]-2-(4-phenyl-piperidin-4-yl)-N-methyl-acetamide;
N-[1-(3,5-Bis-trifluoromethyl-phenyl)-ethyl]-2-(4-phenyl-1-methyl-piperidin-4-yl)-N-methyl-acetamide;
N-[1-(3,5-Dibromo-phenyl)-ethyl]-2-(4-phenyl-piperidin-4-yl)-N-methyl-acetamide;
N-[I'(3,5-Dibromo-phenyl)-ethyl]-2-(4-phenyl-1-methyl-piperidin-4-yi)-N-methyl-acetamide;
N-[1-(3,5-Dibromo-phenyl)-ethyl]-2-[4-(4-fluoro-phenyl)-piperidin-4-yl]-N-methyl-acetamide;
N-[1-(3,5-Dibromo-phenyl)-ethyl]-2-[4-(4-fluoro-phenyl)-1-methyl-piperidin-4-yl]-N-methyl-acetamide;
N[(3,5-Dichlorophenyl)methyl]-2-{4-(4-fluoro-2-methyl-phenyl)-1-[2-(methyloxy)ethyl]-4-piperidinyl}-N-methylacetamide;

N-{1-[3,5-Bis(trifluoromethyl)phenyl]ethyl}-2-[4-(4-fluoro-2-methylphenyl)-4-piperidinyl]-N-methylacetamide;
N-[(3,5-Dibromophenyl)methyl]-2-[4-(4-fluoro-2-methylphenyl)-4-piperidinyl]-N-methylacetamide;
N-{[3,5-Bis(trifluoromethyl)phenyl]methyl}-2-[4-(4-fluoro-2-methylphenyl)-1-methyl-4-piperidinyl]-N-methylacetamide;
N-[(3,5-Dichlorophenyl)methyl]-2-[4-(4-fluoro-2-methylphenyl)-1-methyl-4-piperidinyl]-N-methylacetamide;
N-{[3,5-Bis(trifluoromethyl)phenyl]methyl}-2-[4-(4-fluoro-2-methylphenyl)-4-piperidinyl]acetamide;
N-{[3,5-Bis(trifluoromethyl)phenyl]methyl}-2-[4-(4-fluoro-2-methylphenyl)-1-methyl-4-piperidinyl]acetamide;
N-[(3,5-Dibromophenyl)methyl]-2-[4-(4-fluoro-2-methylphenyl)-1-methyl-4-piperidinyl]-N-methylacetamide;
N-[(3,5-Dibromophenyl)methyl]-N-methyl-2-[4-(2-methylphenyl)-4-piperidinyl]acetamide;
N-[(3,5-Dibromophenyl)methyl]-N-methyl-2-[1-methyl-4-(2-methylphenyl)-4-piperidinyl]acetamide;
N[(3,5-Dichlorophenyl)methyl]-2-[4-(4-fluorophenyl)-1-methyl-4-piperidinyl]-N-methylacetamide;
N-{[3,5-Bis(trifluoromethyl)phenyl]methyl}-2-[4-(4-fluorophenyl)-1-methyl-4-piperidinyl]-N-methylacetamide;
N-[1-(3,5-Dibromophenyl)-1-methylethyl]-2-[4-(4-fluorophenyl)-4-piperidinyl]-N-methylacetamide;
N-[1-(3,5-Dibromophenyl)-1-methylethyl]-2-[4-(4-fluorophenyl)-1-methyl-4-piperidinyl]-N-methylacetamide;
N-[1-(3,5-Bis-trifluoromethyl-phenyl)-ethyl]-2-[4-(4-fluoro-phenyl)-piperidin-4-yl]-N-methyl-acetamide;
N-[1-(3,5-Bis-trifluoromethyl-phenyl)-ethyl]-2-[4-(4-fluoro-phenyl)-1-methyl-piperidin-4-yl]-N-methylacetamide;
2-[1-(Cyclopropylmethyl)-4-(4-fluorophenyl)-4-piperidinyl]-N-[(3,5-dibromophenyl) methyl]-N-methylacetamide;
2-[4-{2-[[(3,5-Dibromophenyl)methyl](methyl)amino]-2-oxoethyl}-4-(4-fluorophenyl)-1-piperidinyl]-N,N-dimethylacetamide;
N-[(3,5-Dibromophenyl)methyl]-2-[1-ethyl-4-(4-fluorophenyl)-4-piperidinyl]-N-methylacetamide;
N-{1-[3,5-Bis(trifluoromethyl)phenyl]ethyl}-2-[4-(4-fluorophenyl) hexahydro-1H-azepin-4-yl]-N-methylacetamide;
N{1-[3,5-Bis(trifluoromethyl)phenyl]ethyl}-2-[4-(4-fluro-phenyl)-1-methylhexahydro-1H-azepin-4-yl]-N-methylacetamide;
N-[(3,5-Dibromophenyl)methyl]-2-[4-(4-fluorophenyl) hexahydro-1H-azepin-4-yl]-N-methylacetamide;
N[(3,5-Dibromophenyl)methyl]-2-[4-(4-fluorophenyl)-1-methylhexahydro-1H-azepin-4-yl]-N-methylacetamide;
N[(3-Bromo-5-cyanophenyl)methyl]-2-[4-(4-fluorophenyl)-4-piperidinyl]-N-methylacetamide;
N[(3-Bromo-5-cyanophenyl)methyl]-2-[4-(4-fluorophenyl)-1-methyl-4-piperidinyl]-N-methylacetamide;
N-[(3,5-Dibromophenyl)methyl]-N-methyl-2-{4[3-(trifluoromethyl)-phenyl]-4-piperidinyl}acetamide;
N-[(3,5-Dibromophenyl)methyl]-N-methyl-2-{1-methyl-4-[3-(trifluoromethyl)phenyl]-4-piperidinyl}acetamide;
N-[(3,5-Dibromophenyl)methyl]-2-[4-(3,4-dimethylphenyl)-4-piperidinyl]-Nmethylacetamide;
N[1-(3,5-Dibromophenyl)ethyl]-2-[4-(3-fluorophenyl)-1-methyl-4-piperidinyl]-N-methylacetamide;
N-[1-(3,5-Dibromophenyl)ethyl]-2-[4-(4-fluoro-3-methy (phenyl)-4-piperidinyl]-N-methylacetamide;
N[1-(3,5-Dibromophenyl)ethyl]-2-[4-(4-fluoro-3-methylphenyl)-1-methyl-4-piperidinyl]-N-methylacetamide;
2-[4-(3-Chlorophenyl0-4-piperidinyl]-N-[1-(3,5-dibromophenyl)ethyl]-N-methylacetamide;
N-[1-(3,5-Dibromophenyl)ethyl]-2-[4-(3,4-difluroophenyl)-4-piperidinyl]-N-methylacetamide;
N[1-(3,5-Dibromophenyl)ethyl]-2-[4-(3,4-difluorophenyl)-1-methyl-4-piperidinyl]-N-methylacetamide;
N[1-(3,5-Dibromophenyl)ethyl]-2-[4-(3-fluorophenyl)-4-piperidinyl]-N-methylacetamide;
N[1-(3,5-Dibromophenyl)ethyl]-2-[4-(3-fluorophenyl)-1-methyl-4-piperidinyl]-N-methylacetamide;
N[1-(3,5-Dibromophenyl)ethyl]-2-[4-(4-fluoro-3-methylphenyl)-4-piperidinyl]-N-methylacetamide;
N[1-(3,5-Dibromophenyl)ethyl]-2-[4-(4-fluoro-3-methylphenyl)-1-methyl-4-piperidinyl]-N-methylacetamide;
2-[4-(3-Chlorophenyl)-4-piperidinyl]-N [1-(3,5-dibromophenyl)ethyl]-N-methylacetamide;
2-[4-(3-Chlorophenyl)-1-methyl-4-piperidinyl]-N [1-(3,5-dibromophenyl)ethyl]-N-methylacetamide;
2-[4-(3-Chlorophenyl)-4-piperidinyl]-N-[1-(3,5-dichlorophenyl)ethyl]-N-methylacetamide;
2-[4-(3-Chlorophenyl)-1-methyl-4-piperidinyl]-N[1-(3,5-dichlorophenyl)ethyl]-N-methylacetamide;
2-[4-(3-Chlorophenyl)-4-piperidinyl]-N-[(3,5-dibromophenyl)methyl]-N-methylacetamide;
N-[1-(3,5-Dichlorophenyl)ethyl]-2-[4-(4-fluoro-3-methylphenyl)-4-piperidinyl]-N-methylacetamide;
N-[(3,5-Dibromophenyl)methyl]-2-[4-(4-fluoro-3-methylphenyl)-4-piperidinyl]-N-methylacetamide;
N-[(3,5-Dibromophenyl)methyl]-2-[4-(4-fluoro-3-methylphenyl)-1-methyl-4-piperidinyl]-N-methylacetamide;
N-[(3,5-Dibromophenyl)methyl]-2-[4-(3-fluorophenyl)-4-piperidinyl]-N-methylacetamide;
N-[(3,5-Dibromophenyl)methyl]-2-[4-(3-fluorophenyl)-l-methyl-4-piperidinyl]-N-methylacetamide;
N-[(3,5-Dibromophenyl)methyl]-2-[4-(3,4-difluorophenyl)-4-piperidinyl]-N-methylacetamide;
N-[(3,5-Dibromophenyl)methyl]-2-[4-(3,4-difluorophenyl)-1-methyl-4-piperidinyl]-N-methylacetamide;
2-[4-(4-Cyanophenyl)-4-piperidinyl]-N-[I-(3,5-dibromophenyl)ethyl]-N-methylacetamide;
[N-(3,5-Dibromo-benzyl)-2-[4-(4-fluoro-phenyl)-1-methyl-piperidin-4-yl]-N-methyl-acetamide;
N-[1-(S)-1-(3,5-Bis-trifluoromethyl-phenyl)-ethyl]-2-[4-(4-fluoro-phenyl)-1-methyl-piperidin-4-yl]-N-methyl-acetamide;
N-[1-(3,5-Dibromo-phenyl)-ethyl]-2-[4-(4-fluoro-phenyl)-1-methyl-piperidin-4-yl]-N-methyl-acetamide (enantiomer 1);
N-[1-(3,5-Dibromo-phenyl)-ethyl]-2-(1-methyl-4-phenyl-piperidin-4-yl)-N-methyl-acetamide (enantiomer 1);
N-[1-(3,5-Dichloro-phenyl)-ethyl]-2-[4-(4-fluoro-phenyl)-1-methyl-piperidin-4-yl]-N-methyl-acetamide (enantiomer 1);

kkk. Compounds of Formula IX as described in WO2003066589, the contents of which are incorporated herein by reference in its entirety:

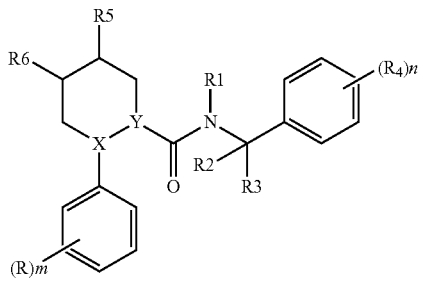

wherein:
R represents halogen or C1-4 alkyl;
R1 represents hydrogen or C1-4 alkyl;
R2 represents hydrogen, C1-4 alkyl or R2 together with R3 represents C3-7 cycloalkyl;
R3 represents hydrogen, C1-4 alkyl, C3-7 cycloalkyl or C3-6 alkenyl; or R1 and R3 together with nitrogen and carbon atom to which they are attached respectively represent a 5 to 6 membered heterocyclic group;
R4 represents trifluoromethyl, C1-4 alkyl, C1-4 alkoxy, trifluoromethoxy or halogen; Rs is hydrogen and R6 is NR7R8 or R5 is NR8R9 and R6 is hydrogen;
R7 represents hydrogen or C1-4 alkyl or R7 and R8 together with nitrogen to which they are attached are a saturated 5 to 7 membered heterocyclic group containing oxygen;
R8 represents hydrogen, phenyl, C3-7 cycloalkyl, (CH2)pC(O)NR10R11, a saturated 5 to 7 membered heterocyclic group containing 1 to 3 heteroatoms selected from oxygen, sulphur and nitrogen and optionally substituted by C1-4 alkyl, S(O)2C1-4 alkyl or C(O)C1-4 alkyl, a 5 membered heteroaryl group containing 1 to 3 heteroatoms selected from oxygen, sulphur and nitrogen and optionally substituted by C1-4 alkyl SO2C1-4 alkyl or C(O)C1-4 alkyl or R8 represents a 6 membered heteroaryl group containing 1 to 3 nitrogen atoms and optionally substituted by C1-4 alkyl, S(O)2C1-4 alkyl or C(O)C1-4 alkyl ; or R8 is a C1-6 alkyl group optionally substituted by one or two groups selected from fluorine, phenyl (optionally substituted by C1-4 alkyl, C(O)C1-4 alkyl or halogen), =O, C3-7 cycloalkyl, hydroxy, amino, dimethylamino, aminocarbonyl, C1-4 alkoxy or trifluoromethyl;
R9 is hydrogen, C1-4 alkyl or R9 and R8 together with nitrogen to which they are attached are a 5 to 7 membered heterocyclic group optionally containing another heroatom selected from oxygen, sulphur and nitrogen and optionally substituted by one or two groups selected from 1l-4 alkyl, =0, S(O)2C1-4 alkyl C(O) C3-7 cycloalkyl or C(O)C1-4 alkyl; R10 and R11 are independently hydrogen or C1-4 alkyl group;
X represents a nitrogen atom and Y is CH or X represents CH and Y is nitrogen;
m is zero or an integer from 1 to 3;
n is an integer from 1 to 3; p is zero, 1 or 2;
4-(S)-Dimethylamino-2-(R)-(4-fluoro-2-methyl-phenyl)-piperidine-1-carboxylic acid[1-(R)-(3,5-bis-trifluoromethyl-phenyl)-ethyl]-methylamide hydrochloride;
4-(S)-Dimethylamino-2-(R)-(4-fluoro-2-methyl-phenyl)-piperidine-1-carboxylic acid (3,5-bis-trifluoromethyl-benzyl)-methylamide hydrochloride;
4-(S)-(2-Fluoroethyl)-amino-2-(R)-(4-fluoro-2-methyl-phenyl)-piperidine-1-carboxylic acid [1-(R)-(3,5-bis)-trifluoromethyl-phenyl)-ethyl]-methylamide hydrochloride;
4-(S)-(2-Fluoro-ethylamino)-2-(R)-(4-fluoro-2-methyl-phenyl)-piperidine-1-carboxylic acid (3,5-bis-trifluoromethyl-benzyl)-methylamide hydrochloride.

lll. Compounds of Formula X as described in WO2003/066621, the contents of which are incorporated herein by reference in its entirety:

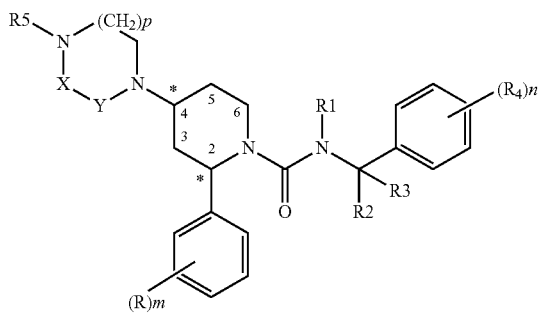

wherein
R represents halogen or C1-4 alkyl;
R1 represents hydrogen or C1-4 alkyl;
R2 represents hydrogen, C1-4 alkyl;
R3 represents hydrogen, C1-4 alkyl;
R4 represents trifluoromethyl, C1-4 alkyl, C1-4 alkoxy, trifluoromethoxy or halogen;
R5 represents hydrogen, C1-4 alkyl, C3-7 cycloalkyl, C(O)R6 or S(O)2R6;
R6 represents C1-4 alkyl or C3-7 cycloalkyl;
m is zero or an integer from 1 to 3;
n is an integer from 1 to 3;
p is an integer from 1 to 2; X and Y are independently C(O) or CH2 provided that i) X and Y are not both C(O) and ii) when X and Y are both CH2 and p is 1, R5 is not hydrogen, C1-4 alkyl or C(O)R6;
including the following named compounds:
2-(R)-(4-Fluoro-2-methyl-phenyl)-4-(R)-(3-oxo-piperazin-1-yl-)-piperidine-1-carboxylic acid, (3,5-bis-trifluoromethyl-benzyl)-methylamide;
2-(R)-(4-Fluoro-2-methyl-phenyl)-4-(S)-(3-oxo-piperazin-1-yl-)-piperidine-1-carboxylic acid, (3,5-bis-trifluoromethyl-benzyl)-methylamide;
2-(R)-(4-Fluoro-2-methyl-phenyl)-4-(R)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-methyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-methyl-3-oxo-piperazin-1-yl)-piperidine-1-carboxylic acid, [1-(R)-(3,5-bis-trifluoromethyl-phenyl)-ethyl]-methylamide;
2-luoro-2-methyl-phenyl)-4-(R)-(2-oxo-piperazin-1-yl)-piperidine-1-carboxylic acid (3,5-bis-trifluoromethyl-benzyl)-methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;
2-(4-Fluoro-2-methyl-phenyl)-4-(S)-(2-oxo-piperazin-1-yl)-piperidine-1-carboxylic acid, (3,5-bis-trifluoromethyl-benzyl)-methylamide;

2-(R)-(4-Fluoro-2-methyl-phenyl)-4-(S)-(2-oxo-4-methyl-piperazin-1-yl)-piperidine-1-carboxylic acid, (3,5-bis-trifluoromethyl-benzyl)-methylamide;
2-(R)-(4-Fluoro-2-methyl-phenyl)-4-(S)-(4-methyl-2-oxo-piperazin-1-yl)-piperidine-1-carboxylic acid, [1-(R)-(3,5-bis-trifluoromethyl-phenyl)-etliyl]-methylamide;
2-(R)-(4-Fluoro-2-methyl-phenyl)-4-(S)-(4-methyl-2-oxo-piperazin-1-yl)-piperidine-1-carboxilic acid, [1-(R)-(3,5-bis-trifluorometliyl-phenyl)-ethyl]-methylamide;
2-(R)-(4-Fluoro-2-methyl-phenyl)-4-(R)-(4-cyclopropyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(4-cyclopropyl-3-oxo-piperazin-1-yl-)-piperidine-1-carboxylic acid, 1-(3,5-bis-trifluoromethyl-benzyl)-methylamide;
2-(R)-(4-Fluoro-2-methyl-phenyl)-4-(S)-(1-methanesulfonyl-piperazin-1-yl)-piperidine-1-carboxylic acid, 1-(3,5-bis-trifluoromethyl-benzyl)-methylamide;
2-(R)-(4-Fluoro-2-methyl-phenyl)-4-(S)-(1-methanesulfonyl-piperazin-1-yl)-piperidine-1-carboxylic acid, 1-[(R)-(3,5-bis-trifluoromethyl-phenyl)-ethyl]-methylamide;
mmm. Compounds of Formula XI as described in WO2004/099143, the contents of which are incorporated herein by reference in its entirety:

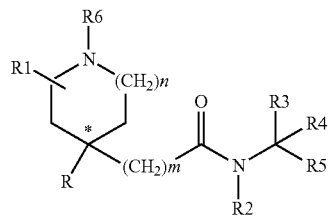

wherein R represents a radical selected from

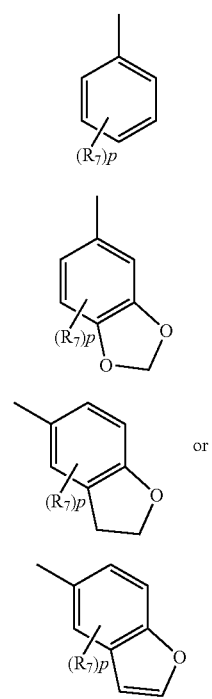

in which $R_7$ is halogen, cyano, C1-4 alkyl, C1-4 alkoxy, trifluoromethyl or trifluoromethoxy;
p is an integer from 0 to 3;
R1 represents hydrogen, halogen, cyano, C2-4 alkenyl, C1-4 alkyl optionally substituted by halogen, cyano or C1-4 alkoxy;
R2 represents hydrogen or C1-4 alkyl;
R3 and R4 independently represent hydrogen, C1-4 alkyl or R3 together with R4 represent C3 7 cycloalkyl;
R5 represents: phenyl substituted by 1 to 3 groups independently selected from trifluoromethyl, C1-4 alkyl, cyano, C1-4 alkoxy, trifluoromethoxy, halogen or (SO)rC1-4 alkyl, naphthyl substituted by 1 to 3 groups independently selected from trifluoromethyl, C1-4 alkyl, cyano, C1-4 alkoxy, trifluoromethoxy, halogen or (SO)rC1-4 alkyl, a 9 to 10 membered fused bicyclic heterocyclic group substituted by 1 to 3 groups independently selected from trifluoromethyl, C1 4 alkyl, cyano, C1-4 alkoxy, trifluoromethoxy, halogen or (SO) rC1 4 aikyl or R5 is a 5 or 6 membered heteroaryl group substituted by 1 to 3 groups independently selected from trifluoromethyl, C1-4 alkyl, cyano, C1-4 alkyl, trifluoromethoxy, halogen or (SO) rC1 4 alkyl;
R6 represents hydrogen or (CH2)qR8;
R8 represents hydrogen, C3-7 cyaloalkyl, C1-4 alkoxy, amine, C1-4 alkylamine, (C1-4 alkyl)2amine, OC(O)NR9R10 or C(O)NR9R10;
R9 and R10 independently represent hydrogen, C1-4 alkyl or C3-7 cycloalkyl;
m represents zero or 1;
n is 1 or 2;
q is an integer from 1 to 4;
r is 1 or 2; provided that when R5 is phenyl substituted by 1 to 3 groups independently selected from trifluoromethyl, C1-4 alkyl, cyano, C1-4 alkoxy, trifluoromethoxy, halogen or (SO) rC1-4 alkyl, R is not the radical i)

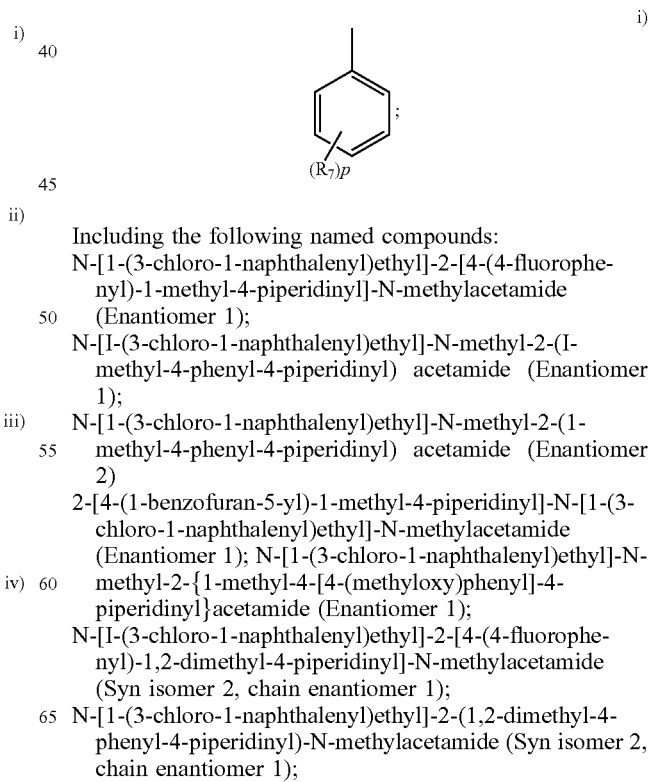

Including the following named compounds:
N-[1-(3-chloro-1-naphthalenyl)ethyl]-2-[4-(4-fluorophenyl)-1-methyl-4-piperidinyl]-N-methylacetamide (Enantiomer 1);
N-[I-(3-chloro-1-naphthalenyl)ethyl]-N-methyl-2-(I-methyl-4-phenyl-4-piperidinyl) acetamide (Enantiomer 1);
N-[1-(3-chloro-1-naphthalenyl)ethyl]-N-methyl-2-(1-methyl-4-phenyl-4-piperidinyl) acetamide (Enantiomer 2)
2-[4-(1-benzofuran-5-yl)-1-methyl-4-piperidinyl]-N-[1-(3-chloro-1-naphthalenyl)ethyl]-N-methylacetamide (Enantiomer 1); N-[1-(3-chloro-1-naphthalenyl)ethyl]-N-methyl-2-{1-methyl-4-[4-(methyloxy)phenyl]-4-piperidinyl}acetamide (Enantiomer 1);
N-[I-(3-chloro-1-naphthalenyl)ethyl]-2-[4-(4-fluorophenyl)-1,2-dimethyl-4-piperidinyl]-N-methylacetamide (Syn isomer 2, chain enantiomer 1);
N-[1-(3-chloro-1-naphthalenyl)ethyl]-2-(1,2-dimethyl-4-phenyl-4-piperidinyl)-N-methylacetamide (Syn isomer 2, chain enantiomer 1);

nnn. Compounds of Formula XII as described in WO2002/081457, the contents of which are incorporated herein by reference in its entirety:

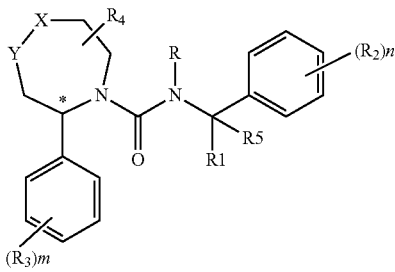

wherein
R represents hydrogen or C1-4alkyl;
R1 represents hydrogen or C1-4 alkyl;
R2 represents trifluoromethyl, C1-4 alkyl, C1-4 alkoxy, trifluoromethoxy or halogen;
R3 represents halogen or C1-4 alkyl;
R4 represents hydrogen, halogen, C1-4 alkyl or C(O)R6;
R5 represents hydrogen, C1-4 alkyl or R5 together within the R1 represents C3-7 cycloalkyl;
R6 represents hydroxy, amino, methylamino, dimethylamino, 5 membered heteroaryl group containing 1 to 3 heteroatoms selected independently from oxygen, sulphur and nitrogen or a 6 membered heteroaryl group containing 1 to 3 nitrogen atoms;
m or n are independently zero or an integer from 1 to 3;
X and Y are independently NR7 or methylene;
R7 represents hydrogen, C1-4 alkyl or C3-7 cycloalkyl provided that when X is NR7, Y is methylene and when X is methylene, Y is NR7;
Including the following named compounds:
2-(S)-(4-Fluoro-2-methyl-phenyl)-[1,4]-diazepane-1-carboxylic acid, (3,5-bis-trifluoromethyl-benzyl)-methylamide;
7-(R)-(4-Fluoro-2-methyl-phenyl)-[1,4]-diazepane-I-carboxylic acid, (3,5-bis-trifluoromethyl-benzyl)-methylamide;
2-(S)-(4-Fluoro-2-methyl-phenyl)-[1,4]-diazepane-1-carboxylic acid, [1-(R)-(3,5-bis-trifluoromethyl-phenyl)-ethyl]-methylamide;
7-(R)-(4-Fluoro-2-methyl-phenyl)-[1,4]-diazepane-1-carboxylic acid, [1-(R)-(3,5-bis-trifluoromethyl-phenyl)-ethyl]-methylamide;
2-(S)-(4-Fluoro-2-methyl-phenyl)-[1,4]-diazepane-1-carboxylic acid, (3,5-dichloro-benzyl)-methylamide;
7-(R)-(4-Fluoro-2-methyl-phenyl)-[1,4]-diazepane-1-carboxylic acid, (3,5-dichloro-benzyl)-methylamide;
2-(S)-(4-Fluoro-2-methyl-phenyl)-[I,4]-diazepane-1-carboxylic acid, [I-(S)-(3,5-bis-trifluoromethyl-phenyl)-ethylJ-methylamide;
7-(R)-(4-Fluoro-2-methyl-phenyl)-[1,4]-diazepane-1-carboxylic acid, [1-(S)-(3,5-bis-trifluoromethyl-phenyl)-ethyl]-methylamide;
2-(S)-(4-Fluoro-2-methyl-phenyl)-[1,4]-diazepane-1-carboxylic acid, (3-chloro-4-fluoro-benzyl)-methylamide;
7-(R)-(4-Fluoro-2-methyl-phenyl)-[1,4]-diazepane-I-carboxylic acid, (2,5-dichloro-benzyl)-methylamide;
2-(S)-(4-Fluoro-phenyl)-[1,4]-diazepane-1-carboxylic acid, (3,5-bis-trifluoromethyl-benzyl)-methylamide;
7-(R)-(4-Fluoro-phenyl)-[1,4]-diazepane-1-carboxylic acid, (3,5-bis-trifluoromethyl-benzyl)-methylamide;
7-(R)-(4-Fluoro-2-methyl-phenyl)-I-methyl-[1,4]-diazepane-I-carboxylic acid, (3,5-dichloro-benzyl)-methylamide;
7-(R)-(4-Fluoro-2-methyl-phenyl)-1-methyl-[1,4]-diazepane-1-carboxylic acid, (3,5-dichloro-benzyl)-methylamide;
7-(R)-(4-Fluoro-2-methyl-phenyl)-1-methyl-[1,4]-diazepane-1-carboxylic acid, [1-(R)-(3,5-bis-trifluoromethyl-phenyl)-ethyl]-methylamide;

ooo. Compounds of Formula XIII as described in WO2004/005255, the contents of which are incorporated herein by reference in its entirety:

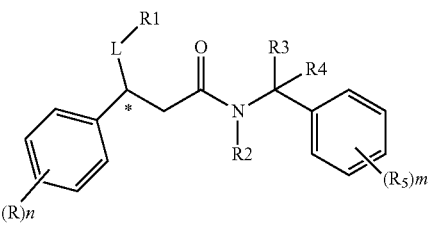

wherein
R represents halogen, C1-4 alkyl, cyano, C1-4 alkoxy, trifluoromethyl or trifluoromethoxy;
R1 represents a 5 or 6 membered heteroaryl group, in which the 5-membered heteroaryl group contains at least one heteroatom selected from oxygen, sulphur or nitrogen and the 6-membered heteroaryl group contains from 1 to 3 nitrogen atoms, or R1 represents a 4,5 or 6 membered heterocyclic group, wherein said 5 or 6 membered heteroaryl or the 4,5 or 6 membered heterocyclic group may optionally be substituted by one to three substituents, which may be the same or different, selected from (CH2)pR6, wherein p is zero or an integer from 1 to 4 and R6 is selected from: halogen, C1-4alkoxy, C1-4alkyl, C3-7cycloalkyl, C1-4 alkyl optionally substituted by halogen, cyano or C1-4 alkoxy, hydroxy, cyano, nitro, trifluoromethyl, carboxy, NH(C1-4 alkyl), N(C1-4 alkYl)2 NH(C3-7 cycloalkyl), N(C1-4 alkyl) (C3-7 cycloalkyl) NH(C1-4alkylOC1-4alkoxy), OC(O)NR7R8, NR8C(O)R7 or C(O)NR7R8;
R2 represents hydrogen, or C1-4 alkyl;
R3 and R4 independently represent hydrogen, C1-4 alkyl or R3 together with R4 represents C3-7 cycloalkyl;
R5 represents trifluoromethyl, S(O)qC1-4 alkyl, C1-4 alkyl, C1-4 alkoxy, trifluoromethoxy, halogen or cyano;
R7 and R8 independently represent hydrogen, C1-4 alkyl or C3-7 cycloalkyl;
L is a single or a double bond; n is an integer from 1 to 3; m is zero or an integer from 1 to 3; q is zero or an integer from 1 to 2; provided that a) when L is a double bond, R1 is not an optionally substituted 5 or 6 membered heteroaryl group, in which the 5-membered heteroaryl group contains at least one heteroatom selected from oxygen, sulphur or nitrogen and the 6-membered heteroaryl group contains from 1 to 3 nitrogen atoms; b) the group R1 is linked to the carbon atom shown as * via a carbon atom; and c) when the heteroatom contained in the group R1 is substituted, p is not zero;
Including the following named compounds:
N-(3,5-Bis-trifluoromethyl-benzyl)-3-(4-fluoro-phenyl)-N-methyl-3-piperidin-4-yl-propionamide;
N-(3,5-Dichloro-benzyl)-3-(4-fluoro-phenyl)-N-methyl-3-piperidin-4-yi-propionamide;

N-[1-(3,5-Dichloro-phenyl)-ethyl]-3-(4-fluoro-phenyl)-N-methyl-3-piperidin-4-yl-propionamide;
N-[1-(3,5-Dichloro-phenyl)-ethyl]-3-(4-fluoro-phenyl)-N-methyl-3-[1-(2-methoxyethyl)-piperidin-4-yl]-propionamide;
N-(3,5-Dichloro-benzyl)-3-(4-fluoro-phenyl)-3-(4-fluoro-piperidin-4-yl)-N-methyl-proprionamide;
N-{(3,5-bis(trifluoromethyl)phenyl]methyll-3-(4-fluoro-phenyl)-N-methyl-3-(I-[2-(methyloxy)ethyl]-4-piperidinyl}propionamide
N-{-1-[3,5-bis(trifluoromethyl)phenyl]ethyl}-3-(4-fluoro-phenyl)-N-methyl-3-(4-piperidinyl) propanamide;
N-{1-[3,5-bis(trifluoromethyl)phenyl]-1-methylethyl}-3-(4-fluorophenyl)-3-(4-piperidinyl) propionamide;
N-{[3-bromo-4-(methyloxy)phenyl]methyl}-3-(4-fluoro-phenyl)-N-methyl-3-(4-piperidinyl) propionamide;
N-[(3,5-dimethylphenyl)methyl]-3-(4-fluorophenyl)-N-methyl-3-(4-piperidinyl) propionamide; N-[(3,4-dibromophenyl)methyl]-3-(4-fluorophenyl)-N-methyl-3-(4-piperidinyl) propionamide; N-[(3-fluoro-2-methylphenyl)methyl]-3-(4-fluorophenyl)-N-methyl-3-(4-piperidinyl) propionamide;
N-{[2-chloro-3-(trifluoromethyl)phenyl]methyl}-3-(4-fluorophenyl)-N-methyl-3-(4-piperidinyl) propionamide;
N-{-1-[3,5-bis(Trifluoromethyl)phenyl]ethyl}-3-(4-fluoro-phenyl)-3-(4-fluoro-4-piperidinyl)-N-methylpropionamide;
N-[(3,5-dibromophenyl)methyl]-3-(4-fluorophenyl)-3-(4-fluoro-4-piperidinyl)-N-methylpropionamide;
N-{-1-[3,5-bis(trifluoromethyl)phenyl]ethyl]-3-(2,4-dichlorophenyl)-3-(4-fluoro-4-piperidinyl)-N-methylpropionamide;
N-{-1-[3,5-bis(trifluoromethyl)phenyl]ethyl}-3-(4-fluoro-2-methylphenyl)-3-(4-fluoro-4-piperidinyl)-N-methylpropionamide;
N-[(3,5-dibromophenyl)methyl]-3-(4-fluoro-2-methylphenyl)-3-(4-fluoro-4-piperidinyl)-N-methylpropionamide;
N-[(3,5-dibromophenyl)methyl]-3-(3,4-dichlorophenyl)-3-(4-fluoro-4-piperidinyl)-N-methylpropionamide;
N-{[3,5-bis(trifluoromethyl)phenyl]methyl}-3-(4-fluoro-phenyl)-3-(4-fluoro-4-piperidinyl)-N-methylpropionamide;
3-(4-chlorophenyl)-N-[(3,5-di bromophenyl)methyl]-3-(4-fluoro-4-piperidinyl)-N-methylpropionamide;
N-{[3,5-bis(trifluoromethyl)phenyl]methyl}-3-(4-fluoro-phenyl)-N-methyl-3-(3-piperidinylidene) propionamide;
N[(3,5-dibromophenyl)methyl]-3-(4-fluorophenyl)-N-methyl-3-(4-piperidinylidene) propionamide;
N-{[3,5-bis(trifluoromethyl)phenyl]methyl}-3-(4-fluoro-2-methylphenyl)-N-methyl-3-(1,2,3,6-tetrahydro-4-pyridinyl) propionamide;
N-{(1R)-1-[3,5-bis(trifluoromethyl)phenyl]ethyl}-3-(4-fluoro-2-methylphenyl)-N-methyl-3-(1,2,3,6-tetrahydro-4-pyridinyl) propionamide;
N-{[3,5-bis(trifluoromethyl)phenyl]methyl}-3-(4-fluoro-phenyl)-N-methyl-3-(3-pyrrolidinyl) propionamide;
N-([3,5-bis(trifluoromethyl)phenyl]methyl}-3-(4-fluoro-phenyl)-3-(3-fluoro-3-piperidinyl)-N-methylpropionamide;
N-{-1-[3,5-bis(trifluoromethyl)phenyl]ethyl}-3-(4-fluoro-phenyl)-N-methyl-3-(2-morpholinyl)propionamide;
N-{[3,5-bis(trifluoromethyl)phenyl]methyl}-3-(4-fluoro-phenyl)-N-methyl-3-(3-piperidinyl)propionamide;
N-{[3,5-bis(trifluoromethyl)phenyl]methyl}-3-(4-fluoro-phenyl)-N-methyl-3-(4-pyridinyl) propionamide;

N-{(1R)-1-[3,5-bis(trifluoromethyl)phenyl]ethyl}-3-(4-fluorophenyl)-N-methyl-3-(4-piperidinyl)propionamide (diastereoisomer 1);
N-{(1S)-1-[3,5-bis(trifluoromethyl)phenyl]ethyl}-3-(4-fluorophenyl)-N-methyl-3-(4-piperidinyl)propionamide (diastereoisomer 2);
N{(1R)-1-[3,5-bis(trifluoromethyl)phenyl]ethyl}-3-(4-fluorophenyl)-3-(4-fluoro-4-piperidinyl)-N-methylpropionamide (diastereoisomer 1;
N[(3,5-dibromophenyl)methyl]-3-(4-fluorophenyl)-3-(4-fluoro-4-piperidinyl)-N-methylpropionamide (enantiomer 2);
N-{[3,5-bis(trifluoromethyl)phenyl]methyl}-3-(4-fluoro-phenyl)-3-(3-fluoro-3-piperidinyl)-N-methylpropionamide (diastereoisomer A);

and NK-1 antagonist compounds disclosed in the following patent applications the contents of which are hereby incorporated herein by reference in their entirety: WO9817660; U.S. Pat. Nos. 5,929,094, 5,877,191, WO00056727, WO04009573, WO00051984, WO01087838, WO02102372, WO02024629, US20050165083, WO06060346, WO06065711, WO07075528, WO06060390, WO07136570 and WO09002770.

Suitably the NK-1 antagonist is not cyclosporin, particularly not cyclosporin A.

Suitably the NK-1 antagonist is not Spantide, particularly not Spantide I.

The NK-1 antagonists according to the invention may optionally be employed in the form of a pharmaceutically acceptable salt including include salts of acidic or basic groups present in NK-1 antagonist compounds of the invention. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate salts. Suitable base salts include, but are not limited to, aluminum, calcium, lithium, magnesium, potassium, sodium, zinc, and diethanolamine salts.

An NK-1 Antagonist of the present invention may optionally be provided in the form of a prodrug i.e. a precursor of a NK1 antagonist that is converted in vivo into an active or more active form ("the parent compound") by metabolic processes or other chemical breakdown event (e.g. hydrolysis). Prodrugs may conveniently be employed in compositions, methods and uses of the invention when they are more soluble than the parent compound. In some embodiments prodrugs of NK-1 antagonists contain one or more phosphate groups not possessed by the parent compound which aid water solubility Pharmaceutical Compositions and Formulations The NK-1 antagonist according to the present invention can be administered by any convenient route, however the preferred route of administration is topically to the ocular surface and specially topically to the cornea.

It is a specific object of the present invention, the use of NK-1 antagonists for the production of an ophthalmic preparation to be administered topically to the eye for the therapy and/or prophylaxis of corneal neovascularization.

Accordingly, in a preferred embodiment, the invention provides a method for preventing and treating corneal neovascularization by local administration (e.g. of an ophthalmic composition) to the cornea of an NK-1 antagonist.

More generally, one preferred embodiment of the present invention is a composition formulated for topical application on a local, superficial and restricted area in the eye and/or the adnexa of the eye comprising an NK-1 antagonist optionally together with one or more one pharmaceutically acceptable additives (such as diluents or carriers).

The ophthalmic compositions of the invention are in the form of solution, emulsion or suspension (collyrium), ointment, gel, aerosol, mist or liniment together with a pharmaceutically acceptable, eye tolerated and compatible with active principle ophthalmic carrier. Also within the scope of the present invention are particular routes for ophthalmic administration for delayed release, e.g. as ocular erodible inserts or polymeric membrane "reservoir" systems to be located in the conjunctiva sac or in contact lenses.

The ophthalmic compositions of the invention are administered topically, e.g., the composition is delivered and directly contacts the eye and/or the adnexa of the eye.

The composition and pharmaceutical compositions containing at least an NK-1 antagonist of the present invention may be prepared by any conventional technique, e.g. as described in Remington: The Science and Practice of Pharmacy 1995, edited by E. W. Martin, Mack Publishing Company, 19th edition, Easton, Pa.

In one embodiment the composition is formulated so it is a liquid comprising a least an NK-1 antagonist in solution or in suspension. The composition may be formulated in any liquid form suitable for topical application such as eyedrops, artificial tears, eye washes, or contact lens adsorbents comprising a liquid carrier such as a cellulose ether (e.g. methylcellulose).

The liquid may be any useful liquid, however it is frequently preferred that the liquid is an aqueous liquid. It is furthermore preferred that the liquid is sterile. Sterility may be conferred by any conventional method, for example filtration, irradiation or heating or by conducting the manufacturing process under aseptic conditions.

The liquid may comprise one or more lipophile vehicles.

In one embodiment of the present invention, the composition is formulated as an ointment. Any ointment components known to a person skilled in the art, which has no detrimental effect on the area being treated, and is applicable in the formulation of compositions and pharmaceutical compositions for topical administration to the eye can be used. For example, one carrier may be a petrolatum carrier.

The pharmaceutical acceptable additives may in general be any conventionally used pharmaceutical acceptable additive, which should be selected according to the specific formulation, intended administration route etc. For example the pharmaceutical acceptable additives may be any of the additives mentioned in Nema et al, 1997. Furthermore, the pharmaceutical acceptable additive may be any accepted additive from FDA's "inactive ingredients list", which for example is available on the internet address http://www.fda.gov/cder/drug/iig/default.htm.

At least one pharmaceutically acceptable diluents or carrier may be a buffer. For some purposes it is often desirable that the composition comprises a buffer, which is capable of buffering a solution to a pH in the range of 5 to 9, for example pH 5 to 6, pH 6 to 8 or pH 7 to 7.5.

However, in other embodiments of the invention the pharmaceutical composition may comprise no buffer at all or only micromolar amounts of buffer.

The buffer may for example be selected from the group consisting of TRIS, acetate, glutamate, lactate, maleate, tartrate, phosphate, citrate, borate, carbonate, glycinate, histidine, glycine, succinate and triethanolamine buffer. Hence, the buffer may be $K_2HPO_4$, $Na_2HPO_4$ or sodium citrate.

In a preferred embodiment the buffer is a TRIS buffer. TRIS buffer is known under various other names for example tromethamine including tromethamine USP, THAM, Trizma, Trisamine, Tris amino and trometamol. The designation TRIS covers all the aforementioned designations.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic, dibasic acids such as aconitic, adipic, ascorbic, carbonic, glutamic, malic, succinic and tartaric, polybasic acids such as citric and phosphoric and bases such as ammonia, diethanolamine, glycine, triethanolamine, and TRIS.

In some embodiments of the invention the pharmaceutically acceptable additives comprise a stabiliser. The stabiliser may for example be a detergent, an amino acid, a fatty acid, a polymer, a polyhydric alcohol, a metal ion, a reducing agent, a chelating agent or an antioxidant, however any other suitable stabiliser may also be used with the present invention.

For example the stabiliser may be selected from the group consisting of poloxamers, Tween-20, Tween-40, Tween-60, Tween-80, Brij, metal ions, amino acids, polyethylene glucol, Triton, and ascorbic acid.

Furthermore, the stabiliser may be selected from the group consisting of amino acids such as glycine, alanine, arginine, leucine, glutamic acid and aspartic acid, surfactants such as polysorbate 20, polysorbate 80 and poloxamer 407, fatty acids such as phosphotidyl choline ethanolamine and acetyltryptophanate, polymers such as polyethylene glycol and polyvinylpyrrolidone, polyhydric alcohol such as sorbitol, mannitol, glycerin, sucrose, glucose, propylene glycol, ethylene glycol, lactose and trehalose, antioxidants such as ascorbic acid, cysteine HCL, thioglycerol, thioglycolic acid, thiosorbitol and glutathione, reducing agents such as several thiols, chelating agents such as EDTA salts, gluthamic acid and aspartic acid.

The pharmaceutically acceptable additives may comprise one or more selected from the group consisting of isotonic salts, hypertonic salts, hypotonic salts, buffers and stabilisers.

In preferred embodiments other pharmaceutically excipients such as preservatives are present. In one embodiment said preservative is a parabene, such as but not limited to methyl parahydroxybenzoate or propyl parahydroxybenzoate.

In some embodiments of the invention the pharmaceutically acceptable additives comprise mucolytic agents (for example N-acetyl cysteine), hyaluronic acid, cyclodextrin, petroleum. Exemplary compounds incorporated to facilitate and expedite transdermal delivery of topical compositions into ocular or adnexal tissues include, but are not limited to, alcohol (ethanol, propanol, and nonanol), fatty alcohol (lauryl alcohol), fatty acid (valeric acid, caproic acid and capric acid), fatty acid ester (isopropyl myristate and isopropyl n-hexanoate), alkyl ester (ethyl acetate and butyl acetate), polyol (propylene glycol, propanedione and hexanetriol), sulfoxide (dimethylsulfoxide and decylmethylsulfoxide), amide (urea, dimethylacetamide and pyrrolidone derivatives), surfactant (sodium lauryl sulfate, cetyltrimethylammonium bromide, polaxamers, spans, tweens, bile salts and lecithin), terpene (d-limonene, alpha-terpeneol, 1,8-cineole and menthone), and alkanone (N-heptane and N-nonane). Moreover, topically-administered compositions comprise surface adhesion molecule modulating agents including, but not limited to, a cadherin antagonist, a selectin antagonist, and an integrin antagonist.

Drug Delivery Devices

In one embodiment, the invention comprises a drug-delivery device consisting of at least an NK-1 antagonist and a pharmaceutically compatible polymer. For example, the composition is incorporated into or coated onto said polymer. The composition is either chemically bound or physically entrapped by the polymer. The polymer is either hydrophobic or hydrophilic. The polymer device comprises multiple physical arrangements. Exemplary physical forms of the polymer device include, but are not limited to, a film, a scaffold, a chamber, a sphere, a microsphere, a stent, or other structure. The polymer device has internal and external surfaces. The device has one or more internal chambers. These chambers contain one or more compositions. The device contains polymers of one or more chemically-differentiable monomers. The subunits or monomers of the device polymerize in vitro or in vivo.

In a preferred embodiment, the invention comprises a device comprising a polymer and a bioactive composition incorporated into or onto said polymer, wherein said composition includes an NK-1 Antagonist, and wherein said device is implanted or injected into an ocular surface tissue, an adnexal tissue in contact with an ocular surface tissue, a fluid-filled ocular or adnexal cavity, or an ocular or adnexal cavity.

Exemplary mucoadhesive polyanionic natural or semi-synthethic polymers from which the device is formed include, but are not limited to, polygalacturonic acid, hyaluronic acid, carboxymethylamylose, carboxymethylchitin, chondroitin sulfate, heparin sulfate, and mesoglycan. In one embodiment, the device comprises a biocompatible polymer matrix that may optionally be biodegradable in whole or in part. A hydrogel is one example of a suitable polymer matrix material. Examples of materials which can form hydrogels include polylactic acid, polyglycolic acid, PLGA polymers, alginates and alginate derivatives, gelatin, collagen, agarose, natural and synthetic polysaccharides, polyamino acids such as polypeptides particularly poly(lysine), polyesters such as polyhydroxybutyrate and poly-.epsilon.-caprolactone, polyanhydrides; polyphosphazines, poly(vinyl alcohols), poly(alkylene oxides) particularly poly(ethylene oxides), poly(allylamines) (PAM), poly(acrylates), modified styrene polymers such as poly(4-aminomethylstyrene), pluronic polyols, polyoxamers, poly(uronic acids), poly(vinylpyrrolidone) and copolymers of the above, including graft copolymers. In another embodiment, the scaffolds may be fabricated from a variety of synthetic polymers and naturally-occurring polymers such as, but not limited to, collagen, fibrin, hyaluronic acid, agarose, and laminin-rich gels.

One preferred material for the hydrogel is alginate or modified alginate material. Alginate molecules are comprised of (1-4)-linked β-D-mannuronic acid (M units) and α L-guluronic acid (G units) monomers which vary in proportion and sequential distribution along the polymer chain. Alginate polysaccharides are polyelectrolyte systems which have a strong affinity for divalent cations (e.g. $Ca^{+2}$, $Mg^{+2}$, $Ba^{+2}$) and form stable hydrogels when exposed to these molecules. See Martinsen A., et al., Biotech. & Bioeng., 33 (1989) 79-89.

The device is administered topically, subconjunctively, or in the episcleral space, subcutaneously, or intraductally. Specifically, the device is placed on or just below the surface of an ocular tissue. Alternatively, the device is placed inside a tear duct or gland. The composition incorporated into or onto the polymer is released or diffuses from the device.

In one embodiment the composition is incorporated into or coated onto a contact lens or drug delivery device, from which one or more molecules diffuse away from the lens or device or are released in a temporally-controlled manner. In this embodiment, the contact lens composition either remains on the ocular surface, e.g. if the lens is required for vision correction, or the contact lens dissolves as a function of time simultaneously releasing the composition into closely juxtaposed tissues. Similarly, the drug delivery device is optionally biodegradable or permanent in various embodiments.

For example, the composition is incorporated into or coated onto said lens. The composition is chemically bound or physically entrapped by the contact lens polymer. Alternatively, a color additive is chemically bound or physically entrapped by the polymer composition that is released at the same rate as the therapeutic drug composition, such that changes in the intensity of the color additive indicate changes in the amount or dose of therapeutic drug composition remaining bound or entrapped within the polymer. Alternatively, or in addition, an ultraviolet (UV) absorber is chemically bound or physically entrapped within the contact lens polymer. The contact lens is either hydrophobic or hydrophilic.

Exemplary materials used to fabricate a hydrophobic lens with means to deliver the compositions of the invention include, but are not limited to, amefocon A, amsilfocon A, aquilafocon A, arfocon A, cabufocon A, cabufocon B, carbosilfocon A, crilfocon A, crilfocon B, dimefocon A, enflufocon A, enflofocon B, erifocon A, flurofocon A, flusilfocon A, flusilfocon B, flusilfocon C, flusilfocon D, flusilfocon E, hexafocon A, hofocon A, hybufocon A, itabisfluorofocon A, itafluorofocon A, itafocon A, itafocon B, kolfocon A, kolfocon B, kolfocon C, kolfocon D, lotifocon A, lotifocon B, lotifocon C, melafocon A, migafocon A, nefocon A, nefocon B, nefocon C, onsifocon A, oprifocon A, oxyfluflocon A, paflufocon B, paflufocon C, paflufocon D, paflufocon E, paflufocon F, pasifocon A, pasifocon B, pasifocon C, pasifocon D, pasifocon E, pemufocon A, porofocon A, porofocon B, roflufocon A, roflufocon B, roflufocon C, roflufocon D, roflufocon E, rosilfocon A, satafocon A, siflufocon A, silafocon A, sterafocon A, sulfocon A, sulfocon B, telafocon A, tisilfocon A, tolofocon A, trifocon A, unifocon A, vinafocon A, and wilofocon A. [144] Exemplary materials used to fabricate a hydrophilic lens with means to deliver the compositions of the invention include, but are not limited to, abafilcon A, acofilcon A, acofilcon B, acquafilcon A, alofilcon A, alphafilcon A, amfilcon A, astifilcon A, atlafilcon A, balafilcon A, bisfilcon A, bufilcon A, comfilcon A, crofilcon A, cyclofilcon A, darfilcon A, deltafilcon A, deltafilcon B, dimefilcon A, droxfilcon A, elastofilcon A, epsilfilcon A, esterifilcon A, etafilcon A, focofilcon A, galyfilcon A, genfilcon A, govafilcon A, hefilcon A, hefilcon B, hefilcon C, hilafilcon A, hilafilcon B, hioxifilcon A, hioxifilcon B, hioxifilcon C, hydrofilcon A, lenefilcon A, licryfilcon A, licryfilcon B, lidofilcon A, lidofilcon B, lotrafilcon A, lotrafilcon B, mafilcon A, mesafilcon A, methafilcon B, mipafilcon A, nelfilcon A, netrafilcon A, ocufilcon A, ocufilcon B, C, ocufilcon D, ocufilcon E, ofilcon A, omafilcon A, oxyfilcon A, pentafilcon A, perfilcon A, pevafilcon A, phemfilcon A, polymacon, senofilcon A, silafilcon A, siloxyfilcon A, surfilcon A, tefilcon A, tetrafilcon A, trilfilcon A, vifilcon A, vifilcon B, and xylofilcon A. Antibody Compositions:

Within the scope of the invention are compositions formulated as a gel or gel-like substance, creme or viscous emulsions. It is preferred that said compositions comprise at least one gelling component, polymer or other suitable agent to enhance the viscosity of the composition. Any gelling component known to a person skilled in the art, which has no detrimental effect on the area being treated, and is applicable in the formulation of compositions and pharmaceutical compositions for topical administration to the skin, eye or mucous can be used. For example, the gelling component may be selected from the group of: acrylic acids, carbomer, carboxypolymethylene, such materials sold by B. F. Goodrich under the trademark Carbopol (e.g. Carbopol 940), polyethylene-polypropyleneglycols, such materials sold by BASF under the trademark Poloxamer (e.g. Poloxamer 188), a cellulose derivative, for example hydroxypropyl cellulose, hydroxyethyl cellulose, hydroxyethylene cellulose, methyl cellulose, carboxymethyl cellulose, alginic acid-propylene glycol ester, polyvinylpyrrolidone, veegum (magnesium aluminum silicate), Pemulen, Simulgel (such as Simulgel 600, Simulgel EG, and simulgel NS), Capigel, Colafax, plasdones and the like and mixtures thereof.

A gel or gel-like substance according to the present invention comprises for example less than 10% w/w water, for example less than 20% w/w water, for example at least 20% w/w water, such as at least 30% w/w water, for example at least 40% w/w water, such as at least 50% w/w water, for example at least 75% w/w water, such as at least 90% w/w water, for example at least 95% w/w water. Preferably said water is deionised water.

Gel-like substances of the invention include a hydrogel, a colloidal gel formed as a dispersion in water or other aqueous medium. Thus a hydrogel is formed upon formation of a colloid in which a dispersed phase (the colloid) has combined with a continuous phase (i.e. water) to produce a viscous jellylike product; for example, coagulated silicic acid. A hydrogel is a three-dimensional network of hydrophilic polymer chains that are crosslinked through either chemical or physical bonding. Because of the hydrophilic nature of the polymer chains, hydrogels absorb water and swell. The swelling process is the same as the dissolution of non-crosslinked hydrophilic polymers. By definition, water constitutes at least 10% of the total weight (or volume) of a hydrogel.

Examples of hydrogels include synthetic polymers such as polyhydroxy ethyl methacrylate, and chemically or physically crosslinked polyvinyl alcohol, polyacrylamide, poly(N-vinyl pyrrolidone), polyethylene oxide, and hydrolyzed polyacrylonithle. Examples of hydrogels which are organic polymers include covalent or ionically crosslinked polysacchahde-based hydrogels such as the polyvalent metal salts of alginate, pectin, carboxymethyl cellulose, heparin, hyaluronate and hydrogels from chitin, chitosan, pullulan, gellan and xanthan. The particular hydrogels used in our experiment were a cellulose compound (i.e. hydroxypropylmethylcellulose [HPMC]) and a high molecular weight hyaluronic acid (HA).

Hyaluronic acid is a polysaccharide made by various body tissues. U.S. Pat. No. 5,166,331 discusses purification of different fractions of hyaluronic acid for use as a substitute for intraocular fluids and as a topical ophthalmic drug carrier. Other U.S. patent applications which discuss ocular uses of hyaluronic acid include Ser. Nos. 11/859,627; 11/952,927; 10/966,764; 11/741,366; and 11/039,192

Formulations of macromolecules for intraocular use are known, See eg U.S. patent application Ser. Nos. 11/370,301; 11/364,687; 60/721,600; 11/116,698 and 60/567,423; 11/695,527. Use of various active agents is a high viscosity hyaluronic acid is known. See eg U.S. patent application Ser. Nos. 10/966,764; 11/091,977; 11/354,415; 60/519,237; 60/530,062, and; 11/695,527.

Sustained release formulations to treat corneal neovascularization as described in WO2010048086 are within the scope if the invention.

Concentration of Active Ingredient and Therapeutic Regimen

Compositions and pharmaceutical compositions according to the present invention, comprise at least one NK-1 antagonist as an active ingredient. The concentration of NK-1 antagonist in said compositions may vary according to the type of administration they are formulated for. The compositions may comprise 0.1 ng/ml to 10 mg/ml, preferably 100 ng/ml to 10 mg/ml, such as 100 µg/ml to 10 mg/ml, preferably 1 mg/ml to 10 mg/ml NK-1 antagonist.

Accordingly, the total dose per day of active principle may comprise 10 ng to 100 mg, preferably 100 ng to 10 mg, preferably 10 µg to 10 mg, preferably 200 µg to 1 mg, preferably 200 µg, of NK-1 antagonist, preferably. Compositions and pharmaceutical compositions for topical delivery to the eye, according to the present invention, comprise at least one NK-1 Antagonist as an active ingredient. The compositions may comprise 0.01 to 50% (weight/volume) of NK-1 Antagonist, preferably 0.05 to 5% (weight/volume), more preferably 0.05 to 1 wt % (weight/volume), or most preferably 0.1 to 2% (weight/volume) of the NK-1 Antagonist, for example the composition may comprise 0.05% (weight/volume), 0.075%(weight/volume), 0.1%(weight/volume), 1%, (weight/volume), 2%(weight/volume, 40% (weight/volume), 5%(weight/volume), of NK-1 antagonist.

According to the present invention "a therapeutically effective amount" of the composition refers to the amount necessary to induce the desired biological effect on the subject in need of treatment.

The compositions and pharmaceutical compositions according to the present invention may be administered once or several times per day, for example they may be administered in the range of 2 to 10 times a day, such as e.g. 2 to 8 times, for example 2 to 6 times, such as 2 to 4 times, such as 2 to 3 times a day.

The compositions according to the present invention may be administrated to the subject for a period of treatment of one or more than one week such as two weeks, three weeks, four weeks, five weeks, six weeks, seven weeks, eight weeks or more than eight weeks. The treatment may be repeated on subjects who relapse.

A further aspect of the present invention relates to a method of treating or ameliorating a medical condition of the eye characterized by the presence of neovascularization of the cornea comprising administration to an animal subject including a human being in need thereof an effective dosage of a composition or a pharmaceutical composition as defined herein above.

Combination Therapy

In one embodiment the treatment or prevention of CNV consists of use of an NK-1 antagonist as sole pharmaceutically active agent.

However in certain embodiments the invention further encompasses the administration of an NK-1 antagonist concurrently with one or more further therapeutically active agents that are administered to the same patient, each active agent being administered according to a regimen suitable for that medicament. This encompasses pre-treatment, simultaneous treatment, sequential treatment, and alternating regimens.

The one or more therapeutically active agents may be administered by the same route as the NK-1 antagonist or by a different route (or by one or more different routes).

At least one of the one or more further therapeutically active agents may, for example. administered topically to the eye.

Examples of such active agents include but are not limited to antivirals, antibacterial agents (such as antibiotics), analgesics, antagonists of inflammatory cytokines, corticosteroids, non-steroidal anti-inflammatory agents, immunosuppressants and anti-fungal agents.

In one specific embodiment, the invention encompasses a method of treating or preventing CNV by administering an NK-1 antagonist concurrently with an antibiotic agent.

In one specific embodiment there is provided a pharmaceutical composition suitable for topical administration to the eye comprising an NK-1 antagonist and an antibiotic agent. Typically such a composition will comprise one or more diluents or carriers which are pharmaceutically acceptable for topical administration to the eye.

In another embodiment, the one or more further therapeutically active agents are selected from VEGF inhibitors, IL1-R inhibitors, immunosuppressants and TNF inhibitors.

In one embodiment of the invention, one of the one or more further therapeutically active agents is an antibiotic such as amikacin, gentamicin, kanamycin, neomycin, netilmicin, streptomycin, tobramycin, teicoplanin, vancomycin, azithromycin, clarithromycin, clarithromycin, dirithromycin, erythromycin, roxithromycin, troleandomycin, amoxicillin, ampicillin, azlocillin, carbenicillin, clozacillin, dicloxacillin, flucozacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, tetracycline, trimethoprim, cotrimoxazole, demeclocycline, soxycycline, minocycline, doxycycline, oxytetracycline or tetracycline.

In a further embodiment of the invention, one of the one or more further therapeutically active agents is an immunosuppressive agent such as cyclosporin A.

In a further embodiment of the invention, one of the one or more further therapeutically active agents is an antagonist of inflammatory cytokines such as antagonist of tumor necrosis factor alpha (TNFα). Exemplary functional blockers of TNFα include, but are not limited to, recombinant and/or soluble TNFα receptors, monoclonal antibodies, and small molecule antagonists and/or inverse agonists. One or more commercially-available TNF-α blocking agents are reformulated for topical administration in this embodiment. Exemplary commercial TNF-α blocking agents used for reformulation include, but are not limited to, etanerept/Embrel, infliximab/Remicade, and adalimumab/Humira.

Alternatively, one of the one or more further therapeutically active agents is an antagonist of an inflammatory cytokine selected from IL-I, IL-2, IL-4, IL-5, IL-6, IL-8, IL-12, IL-17, IL-18 and IL-23.

In a further embodiment of the invention, one of the one or more further therapeutically active agents is an antagonist of one or more member(s) of the vascular epithelial growth factor (VEGF) family. Exemplary members include, but are not limited to, VEGF-A, VEGF-C, VEGFR-2, and VEGFR-3.

Anti-VEGF agents which inhibit either VEGF itself or the VEGF receptor present in the eye in order to thereby prevent angiogenesis, include but are not limited to monoclonal antibodies such as ranibizumab (LUCENTIS®; rhuFab V2) and bevacizumab (AVASTIN®; rhuMab-VEGF), nucleic acids (aptamers such as MACUGEN®, (pegaptanib) a PEGylated RNA aptamer, and siRNAs directed to VEGF RNA). Bevacizumab is a full-length anti-VEGF antibody approved for use in metastatic colon cancer. Ranibizumab is a humanized anti-VEGF monoclonal antibody fragment that inhibits all isotypes of VEGF and pegaptanib is a VEGF-neutralizing aptamer that specifically inhibits one isoform of VEGF (VEGF-165).

Further examples include antibody fragments (e.g. Ranibizumab), small interfering RNA's decreasing expression of VEGFR or VEGF ligand, post-VEGFR blockade with tyrosine kinase inhibitors, Small molecule RTK inhibitors targeting VEGF receptors including PTK787 can also be used In a further embodiment of the invention, one of the one or more further therapeutically active agents is an antagonist of interferon-gamma.

In a further embodiment of the invention, one of the one or more further therapeutically active agents is an antagonist of one or more chemokines and their receptors. Exemplary chemokines and receptors that may be antagonized by a further active agent include chemokine (C—C motif) receptor 1 (CCRI), chemokine (C—C motif) receptor 2 (CCR2), chemokine (C—C motif) receptor 5 (CCR5), chemokine (C—C motif) receptor 7 (CCR7), and chemokine (C—X—C motif) receptor 3 (CXCR3).

EXAMPLES

Experimental Methods
Animals

Male 6- to 8-week-old C57Bl/6 mice (Taconic Farms, Germantown, N.Y.) were used in experiments for Examples 1 to 3. Male 6- to 8-week-old C57Bl/6 mice (Charles River Lab, Calco, Milan, Italy) were used in experiments for Examples 4-6. Prior to pellet implantation or caustication, animals were anesthetized by intraperitoneal injection of ketamine (120 mg/kg) and xylazine (20 mg/kg) before any surgery.

b-FGF Pellet Implantation Angiogenesis Model

This model was employed to assess the effect of pharmaceutically active substances on the angiogenesis component of CNV.

Sustained release b-FGF micropellets (40 ng/pellet) were prepared as described in Azar D T, Am Ophthalmol Soc 2006; 104:264-302.

Briefly, the pellets were implanted through half thickness linear incisions at the center of cornea using a disposable 30 degrees microknife (F.S.T., Foster City, Calif., USA). Lamellar pocket incisions were then made parallel to the corneal plane using a Von Graefe knife (F.S.T., Foster City, Calif., USA) and advanced to the temporal limbus at lateral canthal area. The pellets were positioned into the pocket 1.0 mm apart from the limbal vascular arcade in temporal side, and tetracycline ophthalmic ointment was applied to the eye after pellet implantation to prevent post surgical infections.

Alkali Burn Model

This model was employed to assess the effect of pharmaceutically active substances on the angiogenesis component of CNV in the presence of a strong inflammatory stimulus (Lu P et al, Cornea. 2007 February; 26(2):199-206.)

In fact, the Alkali burn model is considered an inflammation-driven model of neovascularisation, whereby a reduction in inflammatory cell influx is associated with clinical improvement. (Ueno et al. *Invest Ophthalmol Vis Sci.* 2005 November; 46(11):4097-106.)

Mice were anesthetized by intraperitoneal injection of ketamine (120 mg/kg) and xylazine (20 mg/kg) before any surgery. A 2-mm disc of filter paper saturated with 1 N NaOH was placed onto the right cornea of each mouse for 40 seconds, followed by rinsing extensively with phosphate-buffered saline (PBS) for 2 minutes.

Tetracycline ophthalmic ointment was applied topically to the eye after the procedure in Example 2; Tobramicin 0.3% was applied topically to the eye after the procedure in Examples 4-6

In-vivo Imaging, Immunohistochemistry and Morphometry

After taking photographs under the slit lamp, five mice per group were sacrificed 7 days after b-FGF micropellet implantation or caustication, and freshly enucleated eyes were prepared into corneal flat mounts. Immunohistochemical staining was performed with FITC-conjugated CD31/PECAM-1 (rat-anti-mouse antibody; 1:100; Santa Cruz Biotechnology, Santa Cruz, Calif.). Images were taken at 40×, 400× and 600× magnification. To quantify the blood vessels, corneal whole-mounts were covered with mounting medium (Vector, Burlingame, Calif.) and examined by an epifluorescent microscope. For toxicity studies, mice were examined at the slit lamp daily. Animals were sacrificed seven days later and eye bulbs were removed, fixed in 4% paraformaldehyde, cross-sectioned and stained with standard hematoxylin-eosin. At least three to five different corneas were examined; representative data are presented.

Image Analysis

Both slit-lamp and fluorescence microscopy pictures were qualitatively compared for the amount of corneal neovascularization. Gross anatomical alterations such as disruption of epithelial layer, inflammatory cell infiltration, or endothelial cell loss were searched in hematoxylin-eosin cross sections.

Example 1

Inhibition of Corneal Neovascularisation in a Pellet Angiogenesis Model

Male 6- to 8-week-old C57Bl/6 mice were treated to induce neovascularization using Fibroblast Growth Factor (FGF) 80 ng pellet implantation, a non-inflammatory model of corneal neovascularization (see Experimental Methods).

Immediately after pellet implantation, on Day 0, each group received one of the following topical treatments: (1) fosaprepitant (purchased from Universal Drug Store, Canada and diluted as per technical sheet instructions with 0.9% NaCl solution to reach a final concentration of 1 mg/ml) at the concentration of 1 mg/ml (one drop, 50 µl, per instillation, for a total amount of 0.05 mg of active principle per instillation) in the conjunctival sac 4 times per day for 1 week; or (2) phosphate buffered saline PBS as placebo. 5 mice per group were used. After taking photographs at the slit lamp, mice were sacrificed. Immunohistochemical staining was performed with FITC-conjugated CD31/PECAM-1 to reveal corneal neovessels.

Following b-FGF pellet implantation, neovessels are expected to grow from the limbal vessels (i.e. from the periphery of the cornea), towards the pellet, which is placed in the avascular cornea. The extent of neovascularisation is then evaluated.

We observed an obvious difference in corneal neovascularization in fosaprepitant versus placebo treated eyes The area of normally avascular cornea invaded by neovessels was smaller in fosaprepitant treated eyes as opposed to placebo. The density of vascular ramifications was reduced (i.e. the number of vascular branches per surface unit was reduced). At the slit-lamp, florid neovascularization reaching the pellet was present 7 days after implantation in Placebo-treated eyes. In fosaprepitant-treated eyes, less neovascularization was observed. More specifically, the length of the vessels appeared reduced (i.e. vessels did not reach the pellet) and the density of vascular ramification was reduced (i.e. the number of vascular branches per surface unit was reduced). FIG. 1: upper panel. Slit-lamp in-vivo biomicroscopy, note the reduced neovascularization in the treated eye. Middle panel. Cornea whole mounts stained for PECAM to reveal neovessels (magnification 100×). White arrows indicate the pellet. Note the denser neovascular network in the placebo treated eyes. Lower panel. Reduced density of corneal neovascular network following fosaprepitant administration. Magnification 600×.

Example 2

Inhibition of Corneal Neovascularization in a Caustication Neovascularization Model Male 6- to 8-week-old C57Bl/6 mice were treated to induce neovascularization using sodium hydroxide caustication (see Experimental Methods)

Immediately after sodium hydroxide caustication, on Day 0, each group received one of the following topical treatments: (1) fosaprepitant (purchased from Universal Drug Store, Canada and diluted as per technical sheet instructions with 0.9% NaCl solution to reach a final concentration of 1 mg/ml) at the concentration of 1 mg/ml (one drop, 50 µl, per instillation, for a total amount of 0.05 mg of active principle per instillation) in the conjunctival sac 4 times per day for 1 week; or (2) phosphate buffered saline PBS as placebo. 5 mice per group were used. After taking photographs at the slit lamp, mice were sacrificed. Immunohistochemical staining was performed with FITC-conjugated CD31/PECAM-1 to reveal corneal neovessels.

Figure 2:
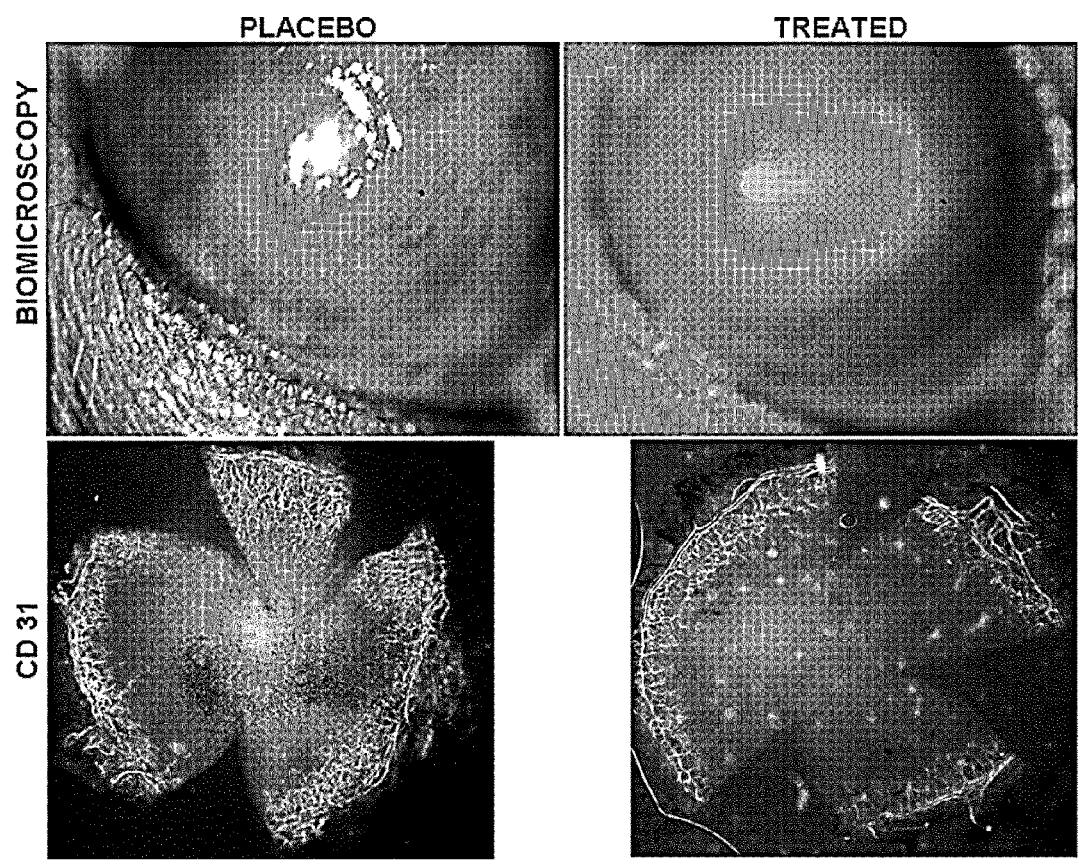
FIG. 2. Topical application of fosaprepitant reduces corneal neovascularization in a mouse caustication angiogenesis assay.

Neovascularization was evident in the cornea at 360 degrees 7 days after caustication in placebo treated eyes, both at the slit lamp and with epifluorescent microscopy (FIG. 2). In eyes treated with fosaprepitant, neovascularization was remarkably reduced. The area of normally avascular cornea invaded by neovessels was smaller in fosaprepitant treated eyes as opposed to placebo. The density of vascular ramifications was reduced (i.e. the number of vascular branches per surface unit was reduced).

Interestingly, we also found that corneal transparency was much improved after fosaprepitant application (i.e. iris was visible), as opposed to placebo-treated corneas, which appeared cloudy (FIG. 2)

Example 3

Toxicity of Fosaprepitant Following Topical Application in Healthy Eyes

Fosaprepitant toxicity was tested on the healthy cornea by administering to 3 healthy C57Bl/6 mice fosaprepitant (purchased from Universal Drug Store, Canada and diluted as per technical sheet instructions with 0.9% NaCl solution to reach a final concentration of 1 mg/ml) at the concentration of 1 mg/ml in the conjunctival sac 4 times per day for 1 week. In vivo corneal biomicroscopy imaging and hematoxylin eosin ocular cross sections were checked as markers for toxicity.

Figure 3:
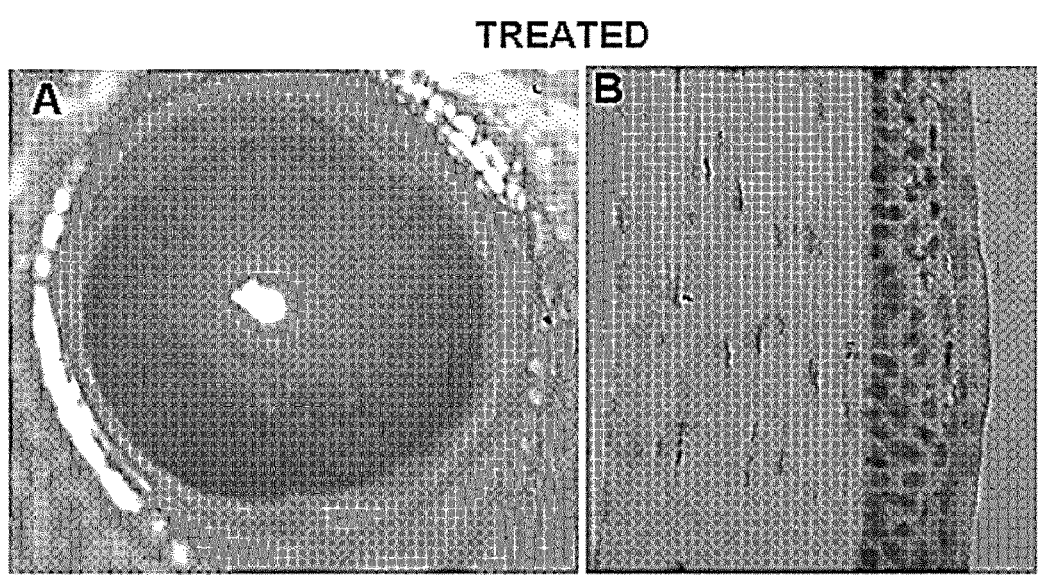
FIG. 3. Topical application of fosaprepitant is not toxic to the cornea.

No alteration of the corneal epithelium, stroma, or endothelium could be found at the slit lamp observation of healthy corneas upon topical fosaprepitant administration for up to 7 days (FIG. 3A). Hematoxylin-eosin staining of eyeball cross-sections appeared normal 7 days after daily administration of fosaprepitant, no anatomical alteration was detected in the epithelium, stroma, or endothelium (FIG. 3B).

FIG. 3A: slit-lamp examination revealed a normal eye.

FIG. 3B: Hematoxylin eosin corneal cross sections showed normal epithelium, stroma and endothelium, magnification 200×.

Conclusion of Examples 1-3

The NK-1 antagonist fosaprepitant—when administered topically to the eye—was effective at preventing/treating CNV in experimental mice models of CNV induced by FGF pellet implantation or sodium hydroxide cauterization. These models were employed, to assess the effect of the drug on the angiogenesis component of CNV, respectively, in the absence and presence of a strong inflammatory stimulus.

Surprisingly, upon observation of corneas in which neovascularization was induced by b-FGF as well as by a proinflammatory stimulus such as sodium hydroxide cauterisation, the NK-1 antagonist treatment led to reduced neovascularisation and improved corneal transparency.

Finally, the drug treatment did not lead to ocular toxicity.

Example 4

Topical Administration to the Eye of Lanepitant Following Alkali Burn Induced Neovascularization of the Cornea Lanepitant (WO9907681) was dissolved in PBS. It was administered topically to the eye with the following dose regimen after alkali burn induced neovascularization of the cornea:

0.4 mg/ml, 6 times a day for 4 days, starting on the day of the tissue injury ("Day 0" to "Day 3").

1.6 mg/ml, 6 times a day for 4 days, starting on the day of the tissue injury ("Day 0" to "Day 3").

6.4 mg/ml, 6 times a day for 4 days, starting on the day of the tissue injury ("Day 0" to "Day 3").

PBS Control, 6 times a day for 4 days, starting on the day of the tissue injury ("Day 0" to "Day 3").

Three mice (for a total of 6 eyes) were treated in each experimental group.

Figure 4A:
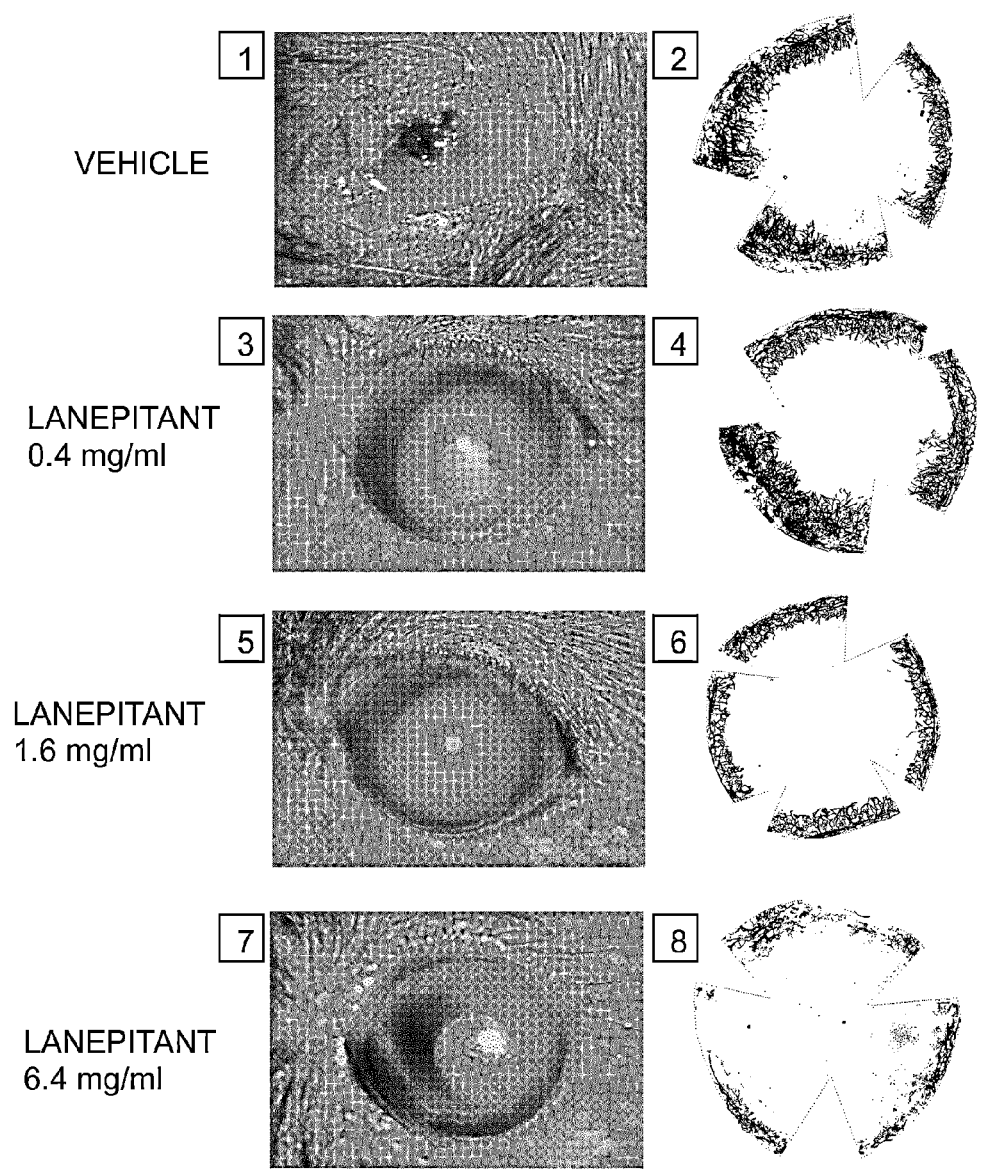
FIG. 4. Topical application of lanepitant reduces corneal neovascularization in a mouse caustication angiogenesis assay.

On Day 4, After taking photographs at the slit lamp, mice were sacrificed. Immunohistochemical staining was performed with FITC-conjugated CD31/PECAM-1 to reveal corneal neovessels (FIG. 4A). Following alkali burn, neovessels are expected to grow from the periphery towards the center of the cornea. The extent of the neovascularization is then evaluated. Briefly, corneas were excised, fixed and stained with FITC-conjugated CD31/PECAM-1 to reveal corneal neovessels. Micro-photographs were taken with the aid of an epifluorescent microscope and mounted to re-create the entire cornea, and skeletonized to form a black and white image as shown in FIG. 4A, right column. The neovascular area was then calculated by measuring the Neovascular Area Index (NV Index). This was obtained by calculating the ratio of the neovascular area—obtained by joining together the inner tip of the neovessels—and the total surface of the cornea (i.e. the total area of the cornea).

As shown in FIG. 4A, treatment with vehicle resulted in corneal perforation, loss of transparence and gross damage to the eyelid (FIG. 4A, Panel 1). However, topical application of an increasing dose of lanepitant resulted in increased corneal transparence; moreover, the anatomy of the eyelids appeared better preserved (FIG. 4A, panels 3, 5, 7).

Figure 4B:
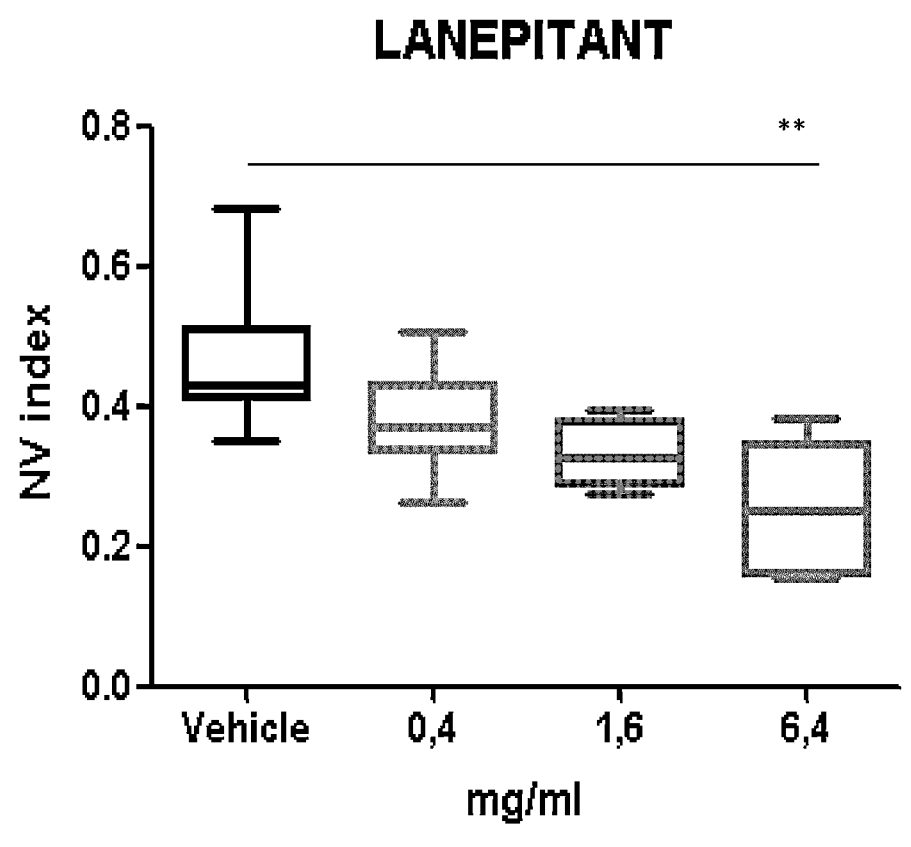

Furthermore, the neovessels progressively reduced with increasing the dose of lanepitant (FIG. 4A, panel 2, 4, 6, 8). This finding was confirmed by the NV Index, progressively reduced with increasing the dose of lanepitant (FIG. 4B); in particular, a dose of 6.4 mg/ml induced a statistically significant reduction compared to vehicle treatment.

Example 5

Topical Administration to the Eye of Befetupitant Following Alkali Burn Induced Neovascularization Befetupitant (WO020008232) was dissolved in DMSO (Dimethyl SulfOxyde). Topical befetupitant was administered to the eye with the following dose regimen after alkali burn induced neovascularization of the cornea:

0.4 mg/ml, 3 times a day for 9 days, starting on the day of the tissue injury.

1.6 mg/ml, 3 times a day for 9 days, starting on the day of the tissue injury.

DMSO control, 3 times a day for 9 days, starting on the day of the tissue injury.

Three mice (for a total of 6 eyes) were treated in each experimental group.

Figure 6A:
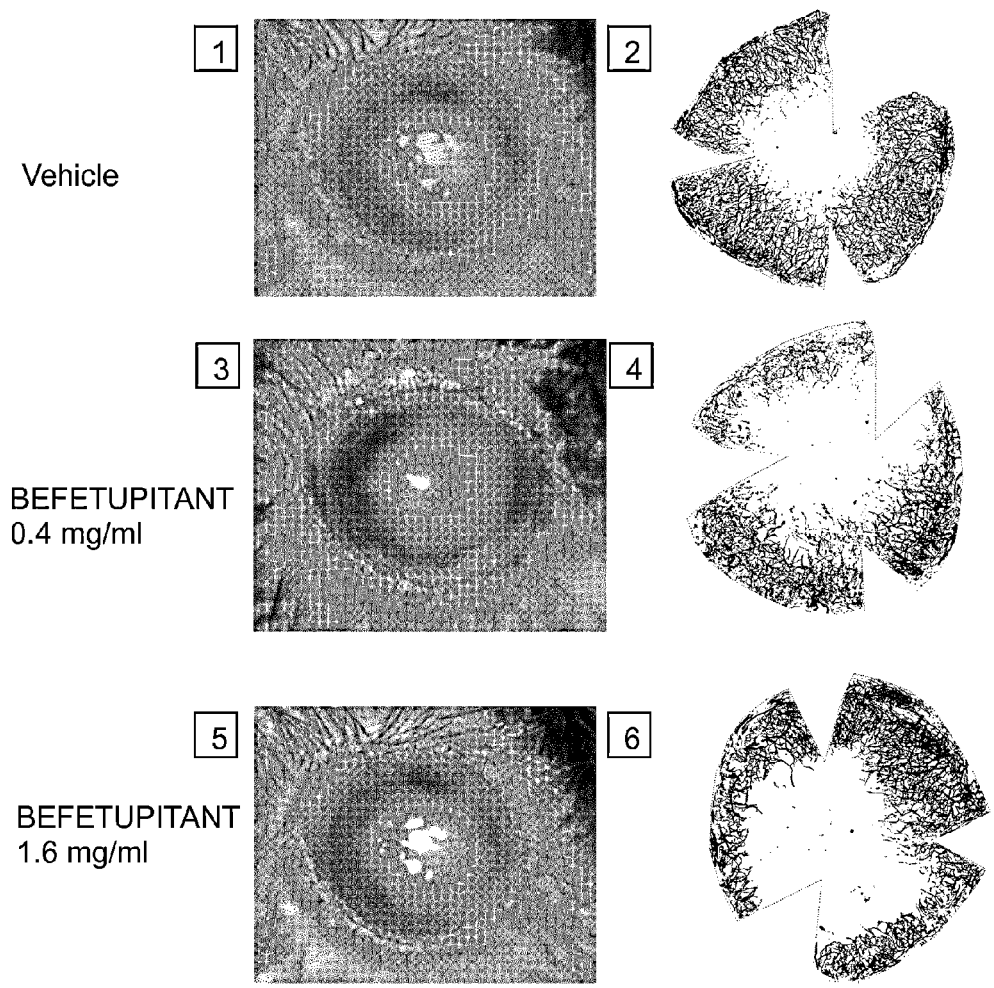
FIG. 6. Topical application of befetupitant reduces corneal neovascularization in a mouse caustication angiogenesis assay.
Figure 6B:
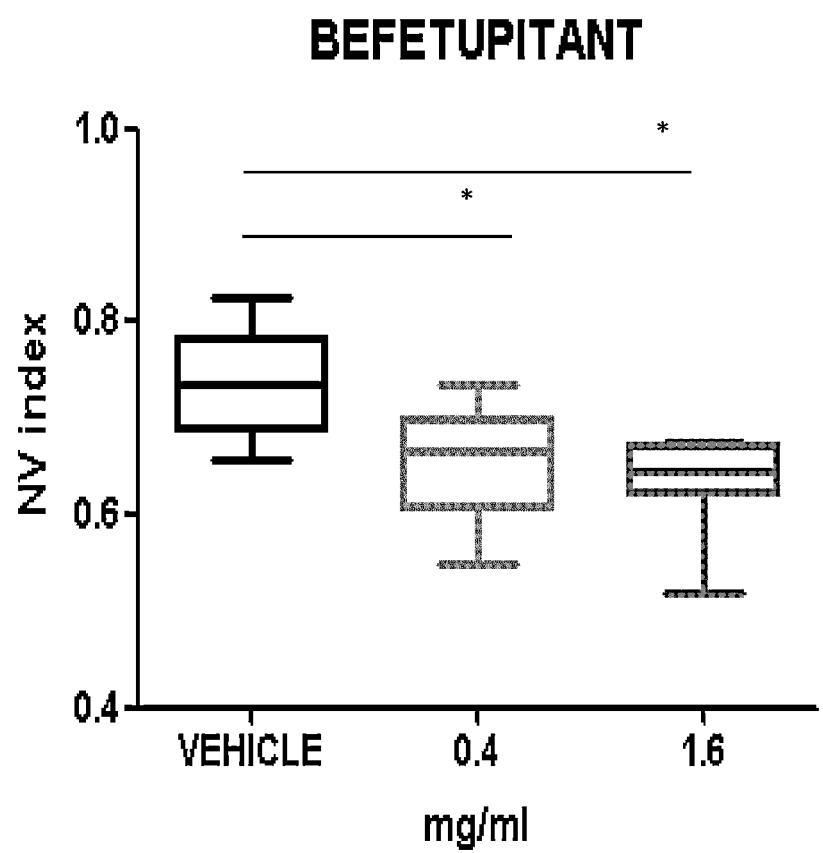

On day 9, after taking photographs at the slit lamp, mice were sacrificed. Immunohistochemical staining was performed with FITC-conjugated CD31/PECAM-1 to reveal corneal neovessels (FIG. 6A). Image analysis was performed as detailed in Example 4. We observed that corneal neovessels were reduced following increasing doses of befetupitant. (FIG. 6A, panels 2, 4, 6). Interestingly, when compared to vehicle-treated animals, both 0.4 mg/ml and 1.6 mg/ml doses of befetupitant achieved a statistically significant reduction in the Corneal Neovascular Index (FIG. 6B).

Example 6

Topical Administration to the Eye of Lanepitant to Prevent and Treat Alkali Burn Induced Neovascularization of the Cornea Topical lanepitant was administered to the eye with the following dose regimen in alkali burn induced neovascularization of the cornea:

1.6 mg/ml lanepitant 6 times a day two days before the injury ("day −3"), two days before the injury ("Day −2"), one day before the procedure ("Day −1"), the day of the procedure ("Day 0"), and 4 days after the injury ("Day 1" through "Day 3") for a total of 8 days of treatment.

Three mice (for a total of 6 eyes) were treated in each experimental group.

Figure 5A:
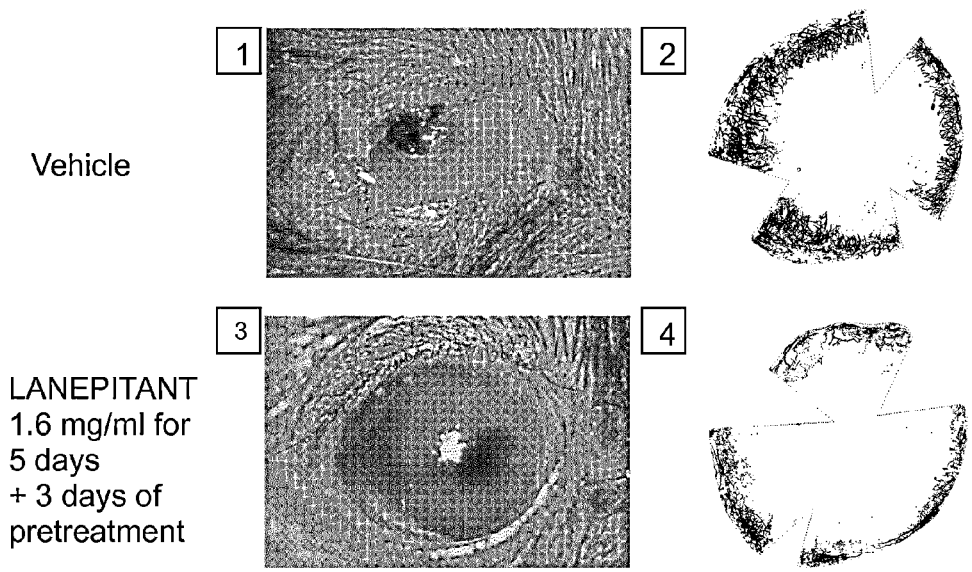
FIG. 5. Topical application of lanepitant reduces corneal neovascularization in a mouse caustication angiogenesis assay when administered before the chemical insult.
Figure 5B:
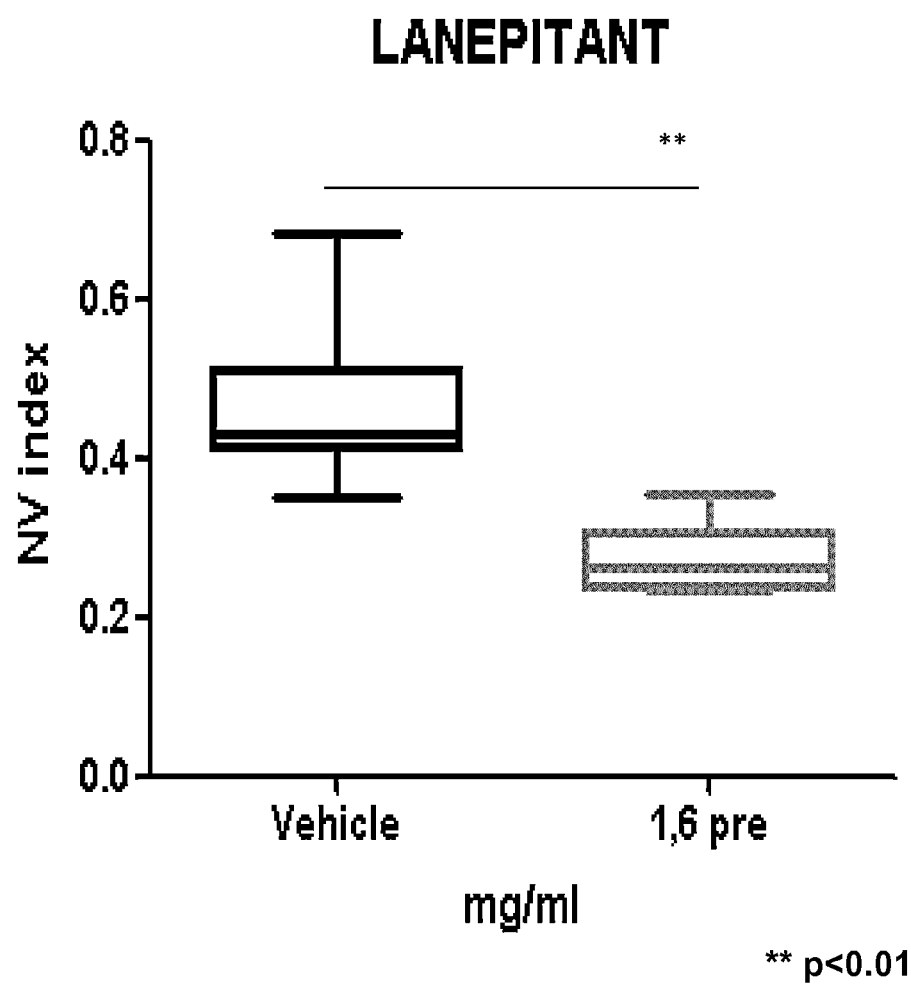

On day 4, after taking photographs at the slit lamp, mice were sacrificed. Immunohistochemical staining was performed with FITC-conjugated CD31/PECAM-1 to reveal corneal neovessels (FIG. 5A) Image analysis was performed as detailed in Example 4. When compared with vehicle treated eyes, corneal neovascularization appeared reduced with lanepitant pre-treatment (FIG. 5A, Panel 2, 4). Interestingly, lanepitant pre-treatment achieved a statistically significant reduction in the Cornea Neovascular Index (FIG. 5B), showing an increased effect on neovascularization compared to the same dose administered after the tissue injury. This demonstrates that NK1 antagonists are efficacious in preventing as well as treating corneal neovascularization.

Conclusion of Examples 4-6

The NK-1 antagonists lanepitant and befetupitant—when administered topically to the eye—were effective at preventing/treating CNV in experimental mice models of CNV induced sodium hydroxide (alkali burn) caustication. This model was employed to assess the effect of the drug on the angiogenesis component of CNV.

Surprisingly, upon observation of corneas in which neovascularization was induced by sodium hydroxide caustication, the NK-1 antagonist treatment led to reduced neovascularization.

Furthermore, while treating the ocular burns resulting from the alkali burn model, interesting novel findings were revealed: corneal perforation was reduced and corneal transparency increased in the eyes treated with NK1 receptor antagonists lanepitant and befetupitant. Furthermore, lid anatomy appeared better preserved, incidence of symblepharon and ankyloblepharon was reduced by treatment with said compounds. (FIG. 4A, panel 3, 5, 7; FIG. 5A, panel 3).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention claimed is:

1. A method of treating corneal neovascularization ("CNV") which comprises administering to a subject in need thereof a therapeutically effective amount of an NK-1 antagonist wherein the NK-1 antagonist is selected from the group consisting of a fosaprepitant, aprepitant, lanepitant and befetupitant and wherein the NK-1 receptor antagonist is administered topically to the cornea.

2. A method according to claim 1 wherein CNV is concurrent or consequential to an inflammatory condition.

3. A method according to claim 1 wherein CNV is caused by one of the following conditions: bacterial infection, viral infection, *Chlamydia trachomatis* infection, infectious keratitis including herpes simplex keratitis, viral interstitial keratitis, infections caused by *staphylococcus, streptococcus, Pseudomonas* or microbial keratoconjunctivitis, *Pseudomonas aeruginosa* infection, chemical or physical insult of the eye, degenerative and traumatic disorders, dry eye, progressive corneal vascularization caused by graft-versus-host disease, limbal stem cell deficiency (including idiopathic, traumatic, aniridia, autoimmune polyendocrinopathy), Stevens-Johnson syndrome, ocular pemphigoid, recurrent pterygium following surgery, extended wearing of hydrogel contact lenses.

4. A method according to claim 1 wherein the NK-1 antagonist is aprepitant or a pharmaceutically acceptable salt thereof.

5. A method according to claim 1 wherein the NK-1 antagonist is befetupitant or a pharmaceutically acceptable salt thereof.

6. A method according to claim 1 wherein the NK-1 antagonist is lanepitant or a pharmaceutically acceptable salt thereof.

7. A method according to claim 1 wherein the NK-1 antagonist is administered in combination, by the same or a different route, with one or more further therapeutically active agents.

8. A method according to claim 7 wherein at least one of the one or more further therapeutically active agents is administered topically to the eye.

9. A method according to claim 1 wherein the NK-1 antagonist is fosaprepitant or a pharmaceutically acceptable salt thereof.

* * * * *